(12) United States Patent
Onishi et al.

(10) Patent No.: US 8,777,964 B2
(45) Date of Patent: Jul. 15, 2014

(54) SUTURE AND LIGATURE DEVICE FOR MEDICAL TREATMENT

(75) Inventors: Norio Onishi, Tokyo (JP); Satoshi Miyamoto, Tokyo (JP); Masayuki Iwasaka, Tokyo (JP)

(73) Assignee: Olympus Corporation (JP)

( * ) Notice: Subject to any disclaimer, the term of this patent is extended or adjusted under 35 U.S.C. 154(b) by 867 days.

(21) Appl. No.: 11/913,986

(22) PCT Filed: May 16, 2006

(86) PCT No.: PCT/JP2006/309689
§ 371 (c)(1),
(2), (4) Date: Nov. 9, 2007

(87) PCT Pub. No.: WO2006/126417
PCT Pub. Date: Nov. 30, 2006

(65) Prior Publication Data
US 2009/0204125 A1    Aug. 13, 2009

(30) Foreign Application Priority Data

May 24, 2005  (JP) ................ P2005-151195
Sep. 13, 2005 (JP) ................ P2005-264816

(51) Int. Cl.
*A61B 17/10* (2006.01)

(52) U.S. Cl.
USPC .......... 606/138; 606/139; 606/144; 606/145; 606/148; 600/567; 600/579

(58) Field of Classification Search
USPC .......... 606/139, 144, 148, 138, 145; 600/550, 600/567, 579
See application file for complete search history.

(56) References Cited

U.S. PATENT DOCUMENTS

| 3,995,619 | A | | 12/1976 | Glatzer |
| 5,242,459 | A | * | 9/1993 | Buelna .................. 606/148 |
| 5,704,943 | A | * | 1/1998 | Yoon et al. ............. 606/139 |
| 5,810,845 | A | * | 9/1998 | Yoon .................... 606/139 |
| 5,855,586 | A | * | 1/1999 | Habara et al. ........... 606/144 |
| 7,094,246 | B2 | * | 8/2006 | Anderson et al. ........ 606/148 |
| 2003/0144673 | A1 | | 7/2003 | Onuki et al. |

FOREIGN PATENT DOCUMENTS

| JP | 4-29210 | 3/1992 |
| JP | 7-223110 | 8/1995 |
| JP | 2000-126924 | 5/2000 |
| JP | 2000-326135 | 11/2000 |

(Continued)

OTHER PUBLICATIONS

International Search Report in corresponding PCT application No. PCT/JP2006/309689 dated Jul. 18, 2006.

(Continued)

*Primary Examiner* — Vy Q Bui
(74) *Attorney, Agent, or Firm* — Ostrolenk Faber LLP

(57) ABSTRACT

A ligature device for medical treatment has an operating device that has a ligature tool for medical treatment fitted onto a distal end portion thereof. The operating device is provided with a cutting member that is able to move freely backwards and forwards and is used to cut a ligature wire of the ligature tool for medical treatment. A distal end side of the cutting member has an inclined end portion that is inclined relative to the direction of forward and backward movement, and a blade portion is provided in this inclined end portion.

5 Claims, 20 Drawing Sheets

(56) References Cited

FOREIGN PATENT DOCUMENTS

| | | |
|---|---|---|
| JP | 2003-204966 | 7/2003 |
| JP | 2004-016309 | 1/2004 |
| JP | 2004-188547 | 7/2004 |
| JP | 2005-7507 | 1/2005 |
| JP | 2005-110983 | 4/2005 |
| WO | WO 03/059174 | 7/2003 |
| WO | WO 2005/034770 | 4/2005 |

OTHER PUBLICATIONS

Office Action issued by the Japanese Patent Office on Mar. 15, 2011 in connection with corresponding Japanese Patent Application No. 2005-264816.

Translation of the Office Action issued by the Japanese Patent Office on Mar. 15, 2011 in connection with corresponding Japanese Patent Application No. 2005-264816.

Search Report issued by European Patent Office on Oct. 1, 2013 in connection with corresponding European application No. EP 06 746 403.2.

* cited by examiner

SUTURE AND LIGATURE DEVICE FOR MEDICAL TREATMENT

CROSS REFERENCE TO RELATED APPLICATION

The present application is a 35 U.S.C. §§371 national phase conversion of PCT/JP2006/309689, filed May 16, 2006, which claims priority of Japanese Patent Application No. 2005-151195, filed May 24, 2005, and Japanese Patent Application No. 2005-264816 filed Sep. 13, 2005, the disclosure of which has been incorporated herein by reference. The PCT International Application was published in the Japanese language.

BACKGROUND OF THE INVENTION

1. Field of the Invention

The present invention relates to a suture and ligature device for medical treatment that is used together with an endoscope in endoscopy treatments such as the suturing or ligaturing of biological tissue in a patient.

Priority is claimed on Japanese Patent Application Nos. 2005-151195, filed May 24, 2005 and 2005-264816, filed Sep. 13, 2005, the contents of which are incorporated herein by reference.

2. Description of Related Art

Among suture and ligature devices for medical treatment that suture or ligature biological tissue in a patient under endoscopic observation there are those that have a sheath that is able to be inserted into the channel of an endoscope, an operating wire that is inserted into the sheath such that it can move freely forwards and backwards, and a ligature tool for medical treatment that is engaged with a hook that is fixed to a distal end of the operating wire.

This ligature tool for medical treatment has a ligature wire in the form of a loop, and a stopper through which the ligature wire is press-inserted. The size of the loop can be adjusted by moving the stopper forwards or backwards along the ligature wire. When a lesion portion is being ligatured, the loop is first placed around the lesion portion. Next, the hook is moved backwards and the stopper is pushed forward relatively towards the lesion portion, thereby reducing the diameter of the loop, and tightly binding the lesioned portion. After this, the ligature wire is cut between the portion that is binding the lesioned portion and the portion that is engaged with the hook, and the ligature wire is left in the patient in a state of ligaturing the biological tissue.

Here, in order that the operation to bind and ligature a lesioned portion using a medical ligature tool and the operation to cut the ligature wire can be performed in successive operations, a cutting member that has a blade portion is provided on the outside of the sheath through which the hook is inserted such that it can move freely backwards and forwards. In addition, a wire holding member that receives the cutting member while holding the ligature wire is provided on the medical ligature tool between the portion that is engaged with the hook and the stopper (see, for example, Patent Document 1: Japanese Unexamined Patent Application, First Publication No. 2003-204966). The blade portion of the cutting member in this case is provided at a right angle to the direction of forward movement of the cutting member. When the blade portion cuts a ligature wire that has been pulled to the outside through a side hole in the wire holding member, the cutting blade makes contact at a right angle to the axial direction of the wire holding member, and the cut is made with the ligature wire sandwiched between the holding member and the cutting blade.

SUMMARY OF THE INVENTION

It is a principal object of the present invention to reduce the cutting force that is required by a cutting member when cutting a suture and ligature member such as a ligature wire and the like, and to reliably and speedily cut the suture and ligature member.

The present invention is a suture and ligature device for medical treatment that includes: a suture and ligature tool for medical treatment that has a suture and ligature member that is formed by a flexible wire material and that sutures or ligatures biological tissue, a fixing member that is able to move freely backwards and forwards relative to the suture and ligature member and that fixes biological tissue in a state in which the biological tissue is sutured or ligatured by the suture and ligature member, and a holding member through which the suture and ligature member is inserted such that it is able to move freely backwards and forwards and that has at least one aperture portion that exposes a portion of the suture and ligature member to the outside; an operating device that has a flexible sheath and a manual operating section; and a cutting member that is provided with a blade portion that is able to make at least one of a forward or backward movement and a rotational movement relatively to the suture and ligature member and that is inclined relative to the forward and backward direction or the rotational direction, and that cuts the suture and ligature member.

In the present invention, it is also possible for the cutting member to have a first blade portion and a second blade portion that face each other, and for the first blade portion and the second blade portion to be arranged such that they approach each other at one end thereof and move away from each other at another end thereof.

In the present invention, it is also possible for the suture and ligature member to have exposed portions where portions of the suture and ligature member are exposed to the outside at two locations, and for the cutting member to have two blade portions that individually cut the respective exposed portions, and for these blade portions to be provided at a distance from each other in the direction of forward and backward movement of the cutting member.

The present invention is a suture and ligature device for medical treatment that includes: a suture and ligature tool for medical treatment that has a suture and ligature member that is formed by a flexible wire material and that sutures or ligatures biological tissue, and that has a fixing member that is able to move freely backwards and forwards relative to the suture and ligature member and that fixes biological tissue in a state in which the biological tissue is sutured or ligatured by the suture and ligature member, with the fixing member being provided with a cutting member and the cutting member having a blade portion that is inclined relative to the forward and backward direction or the rotational direction of the cutting member; and an operating device that has a flexible sheath and a manual operating section.

The present invention is a suture and ligature device for medical treatment that includes: a suture and ligature tool for medical treatment that has a suture and ligature member that is formed by a flexible wire material and that sutures or ligatures biological tissue, a fixing member that is able to move freely backwards and forwards relative to the suture and ligature member and that fixes biological tissue in a state in which the biological tissue is sutured or ligatured by the suture and ligature member, and a holding member through which the suture and ligature member is inserted such that it is able to move freely backwards and forwards and that has at least one aperture portion that exposes a portion of the suture and ligature member to the outside; an operating device that has a flexible sheath and a manual operating section; a cutting member that is able to make at least one of a forward or backward movement and a rotational movement relatively on the suture and ligature member, and that cuts the suture and ligature member; a groove portion that is provided at a predetermined angle relative to the forward and backward direction or the rotational direction of the cutting member on either a distal end of the flexible sheath or on the holding member, or else is provided on the cutting member; and a pin that is provided such that it can slide freely inside the groove portion, wherein when the cutting member is moved forwards or backwards or is rotated relative to the operating device manually by an operator, the blade portion of the cutting member moves in a spiral at the distal end side.

In the present invention, it is also possible for the suture and ligature tool for medical treatment to have an engaging member that engages the suture and ligature member in biological tissue at a distal end of the suture and ligature member, and for there to be provided a puncturing member that houses the engaging member such that the engaging member can be freely inserted therein or removed therefrom, and that punctures biological tissue.

DETAILED DESCRIPTION OF THE INVENTION (First Embodiment)

Figure 1:
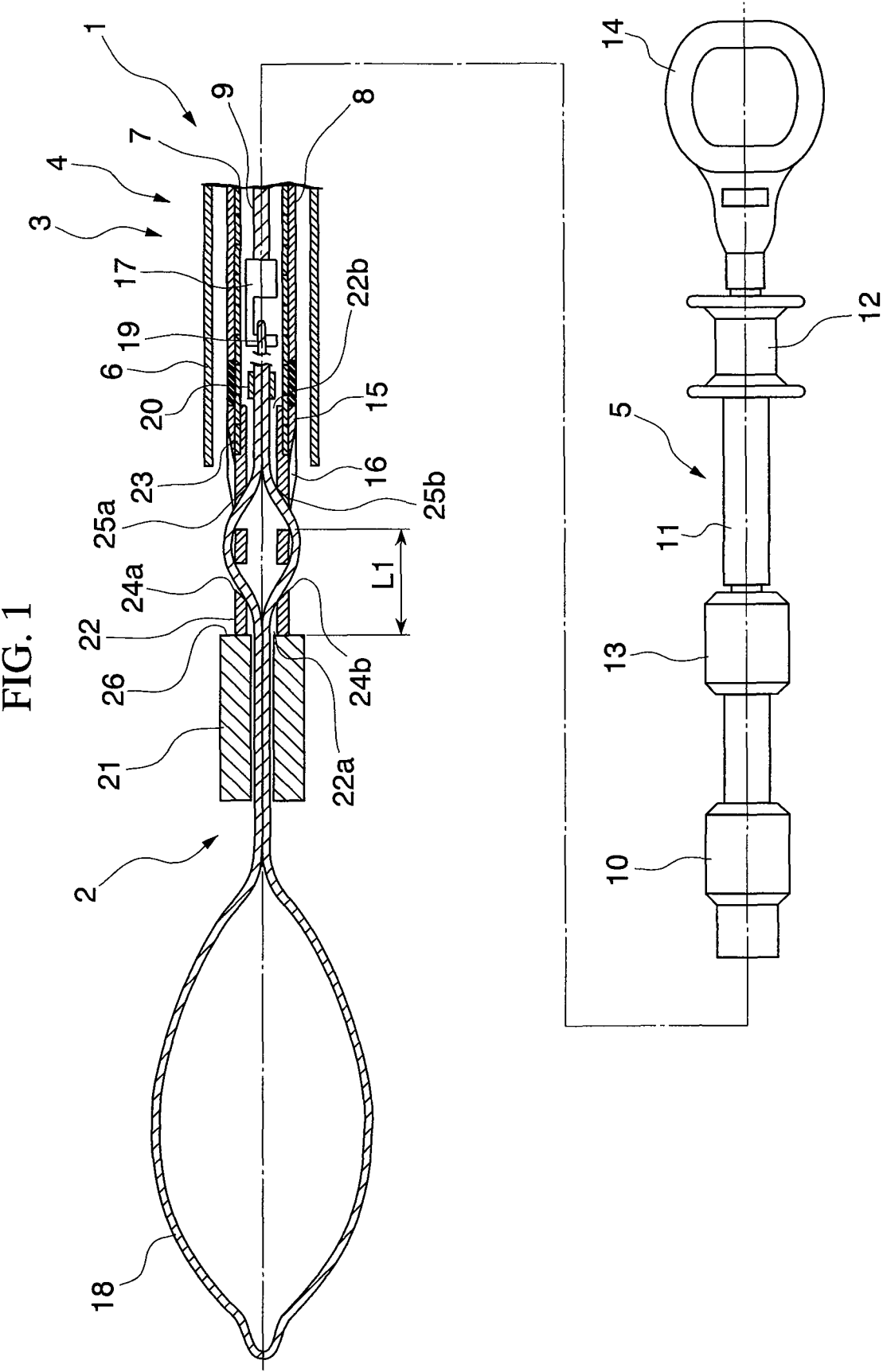
FIG. 1 is a general view of a ligature device for medical treatment according to an embodiment of the present invention.

A first embodiment of the present invention will now be described with reference made to FIG. 1 through FIG. 9. As is shown in FIG. 1, a ligature device for medical treatment 1 is constituted by a ligature tool for medical treatment 2 which is a suture and ligature tool for medical treatment that is left inside a patient's body, and by an operating device 3 onto whose distal end the ligature tool for medical treatment 2 is fitted and that guides the ligature tool for medical treatment 2 into a patient and then performs a ligature operation. The operating device 3 is constituted by an insertion portion 4 which is a flexible sheath that is inserted into a channel of an endoscope, and by a manual operating section 5 that is operated by an operator outside the patient's body.

The insertion portion 4 has an outer sheath 6, an inner sheath 7 that is inserted into the outer sheath 6 and that is able to move forwards and backwards in an axial direction, a cutting sheath 8 that is inserted between the inner sheath 7 and the outer sheath 6 and is able to move forwards and backwards in an axial direction, and an operating wire 9 (i.e., an operating member) that is inserted inside the inner sheath 7 and is able to move forwards and backwards in an axial direction. Furthermore, an engaging member 17 in the shape of a hook is fixed onto a distal end portion of the operating wire 9.

The outer sheath 6 is manufactured from a flexible plastic such as, for example, polyethylene or polytetrafluoroethylene (PTFE) and an outer diameter thereof is φ2 to 5 mm. The inner sheath 7 is manufactured from a flexible plastic such as, for example, polyethylene or PTFE, however, a metal mesh or a metal coil may also be formed inside the plastic. The operating wire 9 is manufactured from a stranded wire made of a metal such as stainless steel. Furthermore, the cutting sheath 8 is manufactured from a flexible plastic such as, for example, polyethylene or PTFE, however, a metal mesh is provided in the interior thereof.

The manual operating section 5 is constituted by a handle 10 that is fixed to a base end portion of the outer sheath 6, a slider 12 that is fixed to a base end portion of the operating wire 9 and is able to move freely backwards or forwards relative to an operating section main body 11, a cutting operating section 13 that is fixed to a base end portion of the cutting sheath 8, and a finger ring 14. The outer sheath 6, the operating wire 9, and the cutting sheath 8 can be moved relatively forwards or backwards in their axial direction by the handle 10, the slider 12, and the cutting operating section 13 respectively.

Figure 2:
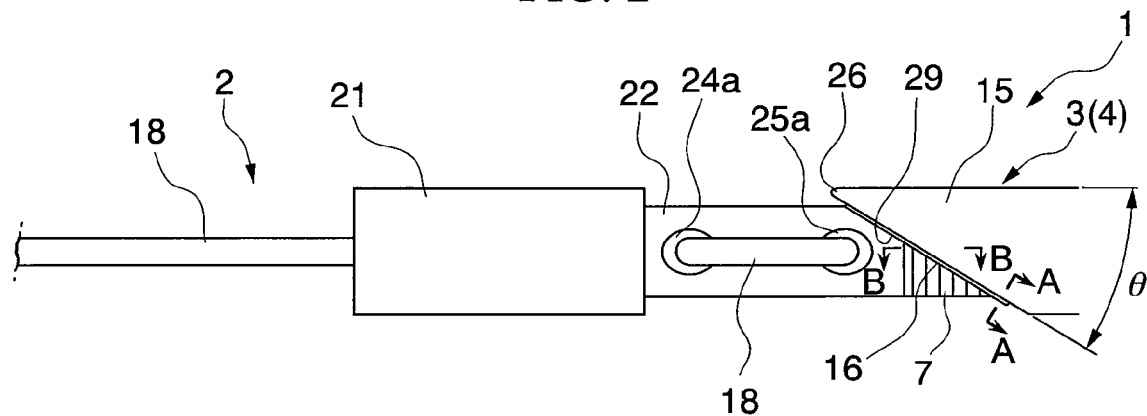
FIG. 2 is a side view showing an enlargement of a distal end portion.

A cutting member 15 is fixed to a distal end portion of the cutting sheath 8 as a device for cutting the ligature tool for medical treatment 2. The cutting member 15 is a toroidal member that is formed by a metal member such as stainless steel and has had its hardness increased as a result of undergoing a heat treatment. As is shown in FIG. 2, an inclined end portion 29 that is inclined relative to the longitudinal axis of the cutting member 15, namely, to the axial line thereof is formed at a distal end of the cutting member 15. A cutting blade 16 that forms an acutely angled blade portion is provided on the inclined end portion 29 except for a distal end portion 26. Note that, as is described below, the axial direction of the cutting member 15 matches the direction of forward and backward movement of the cutting member 15. Accordingly, the cutting blade 16 is a blade portion that is inclined relative to the direction of forward and backward movement of the cutting member 15.

Next, the ligature tool for medical treatment 2 shown in FIG. 1 will be described. A ligature wire 18 which is a flexible wire material (i.e., a suture and ligature member) that ligatures biological tissue is provided at a distal end portion of the ligature tool for medical treatment 2. This ligature wire 18 is folded back substantially in the center in the longitudinal direction thereof to form a loop. The ligature wire 18 is manufactured from a bioresorbable thread such as a nylon (i.e., a polyamide resin) thread, a synthetic resin thread formed from polyolefin or the like, micro wire formed from a metal such as stainless steel, or a silk thread and the thread diameter thereof is between φ0.2 to φ1 mm. This ligature wire 18 is manufactured using any one of a single wire, a stranded wire, or a woven wire. Moreover, of the two base end portions of the ligature wire 18 that are created by the loop, one base end portion is folded back separately from the loop on the distal end side, thereby forming a folded back portion 19 that is able to be engaged with an engaging member 17. Furthermore, in a state in which the respective tips of the two base end portions of the ligature wire 18 are abutting against each other, the two base end portions of the ligature wire 18 are inserted into an inner cavity of a connecting pipe 20 which serves as a fixing tool, and are fixed to the connecting pipe 20 by an adhesive or the like.

Moreover, a cylindrical stopper 21 which is a fixing member that is able to move forwards and backwards along the ligature wire 18 is pressed onto an intermediate portion between the loop portion of the ligature wire 18 and the folded back portion 19 so as to be able to move freely forwards and backwards in the longitudinal direction of the ligature wire 18. This stopper 21 is formed, for example, from a rubber such as silicon rubber or fluorine rubber, or from a type of thermoplastic elastomer, or by knotting the thread. If the stopper 21 is moved forward along the ligature wire 18, then the loop portion that is formed at the distal end of the ligature wire 18 can be contracted, while if the stopper 21 is moved backwards, this loop portion can be enlarged.

Furthermore, a wire holding member 22 that receives the cutting member 15 is provided such that a base end side of the ligature wire 18 that has been pulled through the stopper 21 can be inserted therethrough. This wire holding member 22 is a cylindrical member that is formed from a metal such as stainless steel, or a plastic such as polyolefin, acrylonitrile butadiene styrene (ABS) resin, polyacetal, and polycarbonate or the like. A contracted diameter portion 23 is formed at the base end portion of the wire holding member 22. This contracted diameter portion 23 is inserted inside the inner sheath 7 so as to be supported at the distal end portion of the inner sheath 7. The outer diameter of the wire holding member 22 is substantially the same as the outer diameter of the inner sheath 7 excluding the contracted diameter portion 23. Accordingly, in a state in which the wire holding member 22 is engaged and held in the inner sheath 7, there is no height difference between the outer circumferential surface of the inner sheath 7 and the outer circumferential surface of the wire holding member 22, and the cutting sheath 8 is able to move smoothly backwards and forwards.

Note that distal end side holes 24a and 24b which are a pair of aperture portions through which the ligature wire 18 is able to be inserted are formed in the distal end side of the wire holding member 22. Moreover, a pair of base end side holes 25a and 25b which are a pair of aperture portions through which the ligature wire 18 is able to be inserted are formed from the distal end side holes 24a and 24b to the contracted diameter portion 23. The distal end side hole 24a and the base end side hole 25b are positioned to the front and rear in the axial direction of the wire holding member 22, while, in the same way, the distal end side hole 24b and the base end side hole 25a are also positioned to the front and rear in the axial direction. Furthermore, inner side surfaces on the distal end side of the distal end side holes 24a and 24b and inner side surfaces on the base end side of the base end side holes 25a and 25b are formed as inclined surfaces which open up as they move towards the inner circumferential side of the wire holding member 22 so that the ligature wire 18 is easily inserted and easily removed.

The ligature wire 18 which has been withdrawn from the inner cavity of the stopper 21 is inserted into this wire holding member 22. Specifically, both base end portions of the ligature wire 18 are pulled in a bundled state from a distal end side aperture 22a into the interior of the wire holding member 22, and are then pulled to the outer side of the wire holding member 22 with one wire respectively passing through the distal end side holes 24a and 24b. The wires then pass along the outer circumference of the wire holding member 22 and are drawn once again to the inner side of the wire holding member 22 through the respective base end side holes 25a and 25b that are placed longitudinally in the axial direction.

The wires are then pulled in a bundled state from a base end side aperture 22b. Note that the entire length of the wire holding member 22 is set, for example, to approximately 5 to 10 mm. Because a dimension L1 between a distal end surface of the wire holding member 22 and the base end side holes 25a and 25b is substantially equal to the length of the ligature wire 18 that is left inside a patient at the time of a cutting operation, it is desirable for the dimension L1 to be on the small side, and it may be set, for example, to approximately 2 to 5 mm. Moreover, the portion of the ligature wire 18 that is drawn from the respective side holes 24a, 24b, 25a and 25b to the outer circumferential side of the wire holding member 22 becomes an exposed portion of the ligature wire 18.

Figure 3:
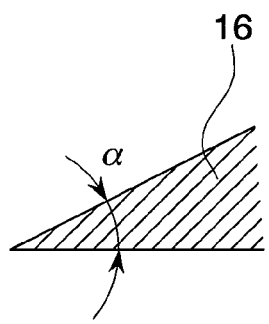
FIG. 3 is a cross-sectional view taken along a line A-A in FIG. 2.
Figure 4:
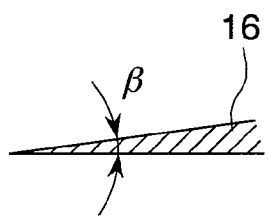
FIG. 4 is a cross-sectional view taken along a line B-B in FIG. 2.
Figure 6:
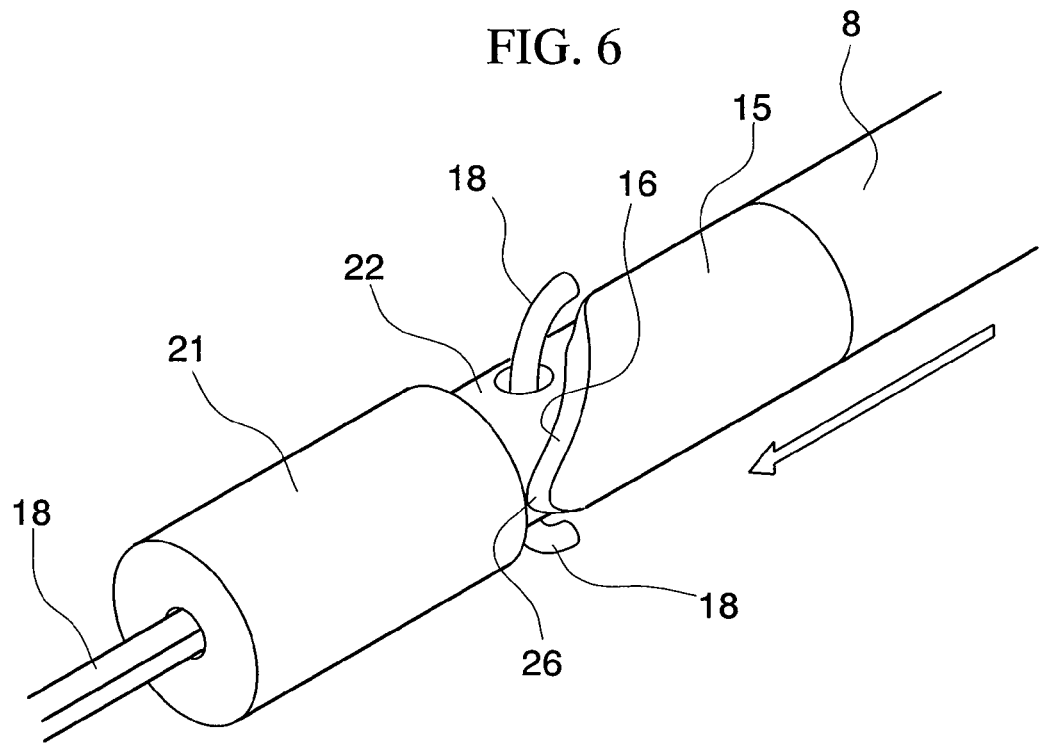
FIG. 6 is a perspective view showing an enlargement of a distal end portion, and shows a ligature wire being cut.

Here, as is shown in FIG. 2 and FIG. 6, an angle $\theta$ of the inclined end portion 29 of the cutting member 15 is set such that, in a state in which the distal end portion 26 where the cutting blade 16 is not formed is abutting against the base end surface of the stopper 21 which has a larger diameter than the wire holding member 22, the cutting blade 16 does not touch the distal end side holes 24a and 24b of the wire holding member 22. As is shown in FIG. 2, the angle $\theta$ of the inclined end portion 29 is an acute angle and is desirably within a range of, for example, 5° to 15°. In contrast, as is shown in FIG. 3 (which is a cross-sectional view taken along the line A-A in FIG. 2), a blade angle $\alpha$ of the cutting blade 16 is an acute angle that faces towards the ligature wire 18 such that it is able to cut the ligature wire 18, and this angle is desirably within a range of, for example, 30° to 35°. Note that, when a direction that is perpendicular to the end surface of the inclined end portion 29 of the cutting member 15 is taken as a reference, the blade angle $\alpha$ is the inclined angle of the cutting blade 16. The actual angle of the cutting blade 16 becomes a blade angle $\beta$ (see FIG. 4 which is a cross-sectional view taken along a line B-B in FIG. 2) because of the angle $\theta$ of the inclined end portion 29 and the blade angle $\alpha$. This blade angle $\beta$ is a smaller angle than the blade angle $\alpha$.

Figure 7:
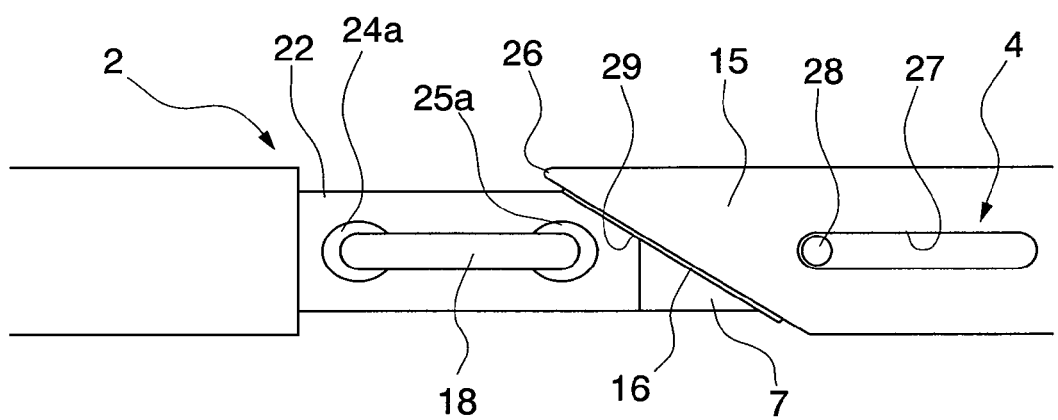
FIG. 7 is a view showing an embodiment that is provided with a guide groove for guiding the cutting member and with a guide pin.

Note that, as is shown in FIG. 7, it is also possible for a guide groove 27 which is a groove portion that is parallel to the axial direction to be provided in the cutting member 15, and for a guide pin 28 that has a slightly smaller diameter than the width of the guide groove 27 and that is able to slide smoothly inside the guide groove 27 to be provided on an outer circumferential portion of the inner sheath 7 so as to protrude outwards in the radial direction of the inner sheath 7. By causing the guide pin 28 to move inside the guide groove 27, any rotation of the cutting member 15 is restricted and only movement in a forward or backward direction is allowed.

Next, an operation of this embodiment will be described.

Figure 8:
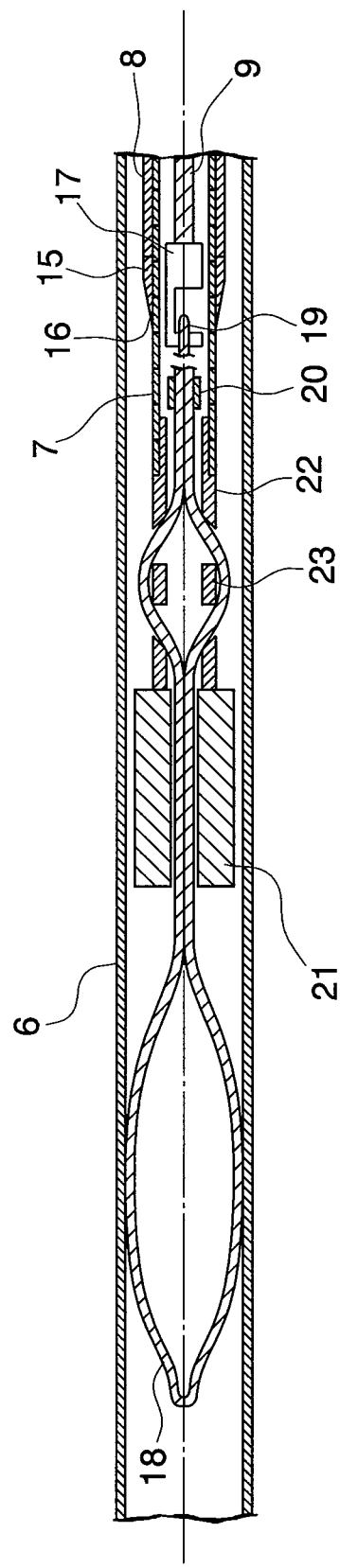
FIG. 8 is a cross-sectional view showing a suture and ligature tool housed within an external sheath.

Firstly, the slider 12 is operated so that the operating wire 9 is moved forward and the engaging member 17 is made to protrude from the distal end apertures of the outer sheath 6 and the inner sheath 7. In this state, the folded back portion 19 of the base end portion of the ligature wire 18 is made to catch on the hook portion of the engaging member 17. When the slider 12 is operated so that the operating wire 9 is moved backward and the engaging member 17 is pulled back inside the inner sheath 7, the contracted diameter portion 23 of the wire holding member 22 enters into the inner sheath 7. As a result, the wire holding member 22 is supported by the distal end portion of the inner sheath 7. In this state, if the handle 10 is operated so that the outer sheath 6 is made to move forward, as is shown in FIG. 8, the ligature wire 18 is housed inside the outer sheath 6 and the loop portion is made narrower.

Figure 9:
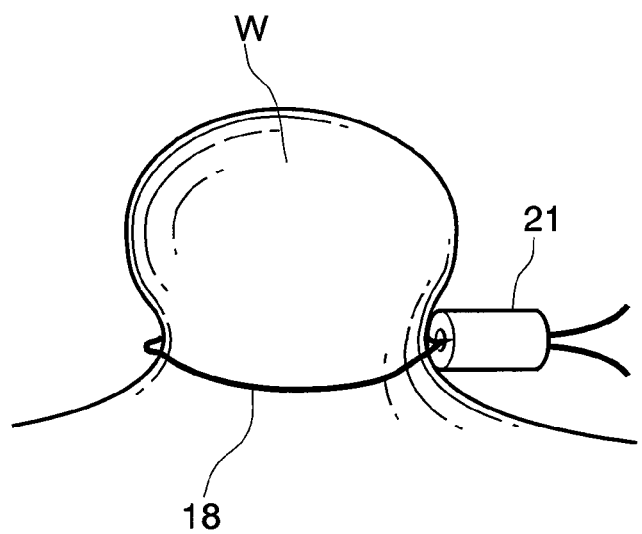
FIG. 9 is a view showing a lesion portion being ligatured.

In this state, the insertion portion 4 is inserted into the channel of an endoscope and this endoscope is then inserted into a body cavity. The distal end portion of the insertion portion 4 is then guided to the target position that is to be treated. While a lesion portion W which is biological tissue such as a polyp or the like such as that shown in FIG. 9 is being monitored using the endoscope, if the handle 10 is operated so that the outer sheath 6 is moved backwards, the ligature wire 18 is made to protrude from the distal end aperture of the outer sheath 7 and, as is shown in FIG. 1, the loop portion of the ligature wire 18 is elastically restored and the diameter thereof is enlarged.

Next, after the loop portion of the ligature wire 18 has been placed around the base portion of the lesion portion W as the lesion portion W is being monitored using the endoscope, the slider 12 is operated so that the operating wire 9 is moved backwards. The base end portion of the ligature wire 18 is pulled inside the inner sheath 7 via the engaging member 17, and the stopper 21 and the wire holding member 22 are moved relatively in the direction of the distal end of the ligature wire 18. As a result, the diameter of the loop portion of the ligature wire 18 is contracted, as is shown in FIG. 9, so that the lesion portion W is tightly bound. As a result of this ligaturing, the flow of blood to the lesion portion W is stopped.

Figure 5:
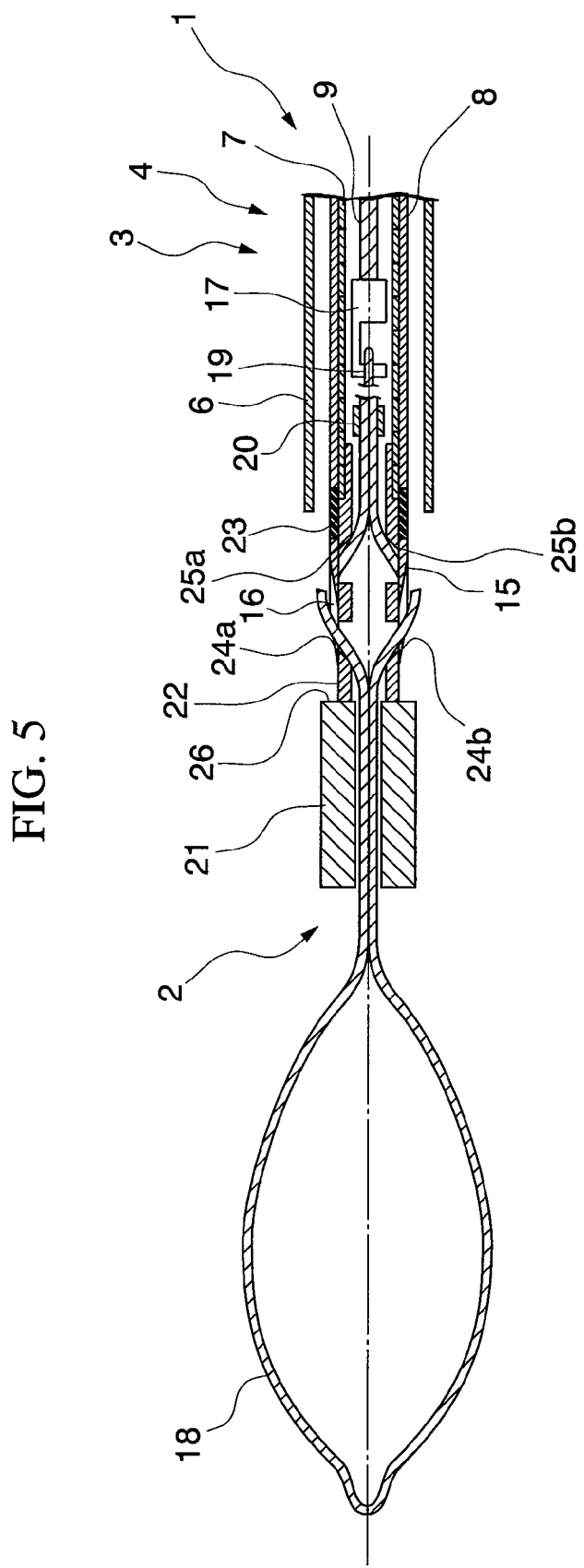
FIG. 5 is a cross-sectional view showing a state in which a ligature wire has been cut.

If, while the slider 12 is being held, the cutting operation section 13 is operated so that the cutting sheath 8 is moved forward, the cutting sheath 8 moves forward while being guided by the inner sheath 7 and slides along while fitting gently into the base end portion of the wire holding member 22. As a result of this, the distal end side of the cutting blade 16 on the inclined end portion 29 comes up against the exposed portion of the ligature wire 18 that is exposed from the respective side holes 24a, 24b, 25a, and 25b. Next, as is shown in FIG. 5, the ligature wire 18 is cut by the cutting blade 16 as the cutting member 15 gradually moves forward. The cutting member 15 moves forwards until the distal end portion 26 thereof abuts against the stopper 21. At this time, the actual blade angle of the cutting blade 16 as seen from the ligature wire 18 becomes the blade angle $\beta$ which is more acute than the blade angle $\alpha$. Because of this blade angle $\beta$ the base end portion side of the ligature wire 18 which had been inserted in the wire holding portion 22, as is shown in FIG. 5, is cut in the vicinity of the base end side holes 25a and 25b. Note that because the cutting blade 16 is not provided at the distal end portion 26 of the cutting member 15, even if it comes up against the stopper 21, as is shown in FIG. 6, there is no damage to the stopper 21.

When the ligature wire 18 is cut, the inner sheath 7 which hitherto was being pulled via the ligature wire 18 is separated from the wire holding member 22. As a result, the ligature tool for medical treatment 2 and the operating device 3 become completely separated from each other. Accordingly, when the insertion portion 4 is withdrawn from the channel of the endoscope, the wire holding member 22 falls from the cut end portion of the ligature wire 18 and, as is shown in FIG. 9, only the ligature wire 18 which was held in a tightly bound state by the stopper 21 is left behind in the patient. As a result, the operation to tightly bind the lesion portion W is ended. The wire holding member 22 which has come free from the ligature wire 18 is discharged naturally to the outside of the body via the digestive tract.

According to this embodiment, because the inclined end portion 29 which has the angle $\theta$ is provided at the distal end of the cutting member 15, and because the cutting blade 16 which has the blade angle $\alpha$ relative to this inclined end portion 29 is provided, due to this angle $\theta$, the actual blade angle $\beta$ when the ligature wire 18 is being cut can be made smaller than the blade angle $\alpha$. Accordingly, because it is possible to perform a cutting operation using this sharp cutting portion, it is possible to reduce the amount of cutting force that it is required in order to cut the ligature wire 18, and the ligature wire 18 can be reliably cut. By employing this type of structure, the ligature wire 18 can be cut easily and operability can be improved without the cutting sheath 8 having to be repeatedly pressed against the ligature wire 18. If, as is the case conventionally, the cutting blade 16 is not provided along the inclined surface portion 29, and a cutting blade is provided on a plane which is perpendicular to the direction of forward and backward movement, then if an attempt is then made to create an acute blade angle, not only is this processing is extremely difficult, but the distal end of the blade becomes extremely thin. Because of this, there is a possibility that the blade will break during a cutting operation. However, in the present embodiment, it is possible to manufacture a cutting member that makes it possible to easily cut the ligature wire 18 without this type of problem arising.

Moreover, conventionally, in order to transmit the force that is imparted to the cutting operation section 13 directly to the cutting blade 16 and reliably cut the ligature wire 18, it has been necessary to increase the rigidity of the cutting sheath 18 or increase the thickness of the cutting sheath 18. This has made insertion into an endoscope difficult and has also led to an increase in manufacturing costs. However, in this embodiment, because such problems do not arise, the insertion into an endoscope is easy and manufacturing costs can also be kept low.

Note that, as is shown in FIG. 7, when the rotation of the cutting member 15 is restricted by the guide groove 27 of the cutting member 15 and the guide pin 28 of the inner sheath 7, because the actual blade angle θ during the cutting of the ligature wire 18 can be easily secured and maintained, the ligature wire 18 can be cut reliably and simply.

(Second Embodiment)

A second embodiment of the present invention will now be described in detail with reference made to FIG. 10 through FIG. 14. This embodiment has the feature that the structure of the cutting member is different. Accordingly, the same symbols are used for member elements that are the same as those in the first embodiment, and any repeated description thereof is omitted.

Figure 10:
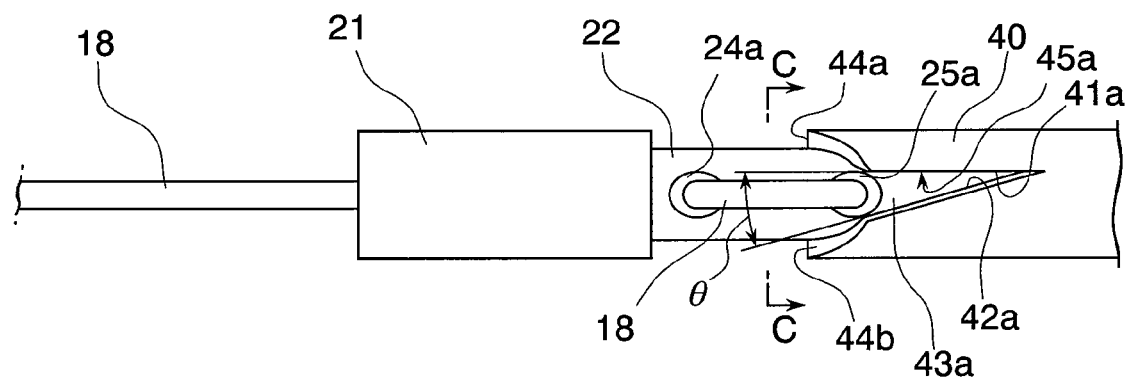
FIG. 10 is a view showing a cutting blade provided on the edge portion of one side of a V shape.
Figure 11:
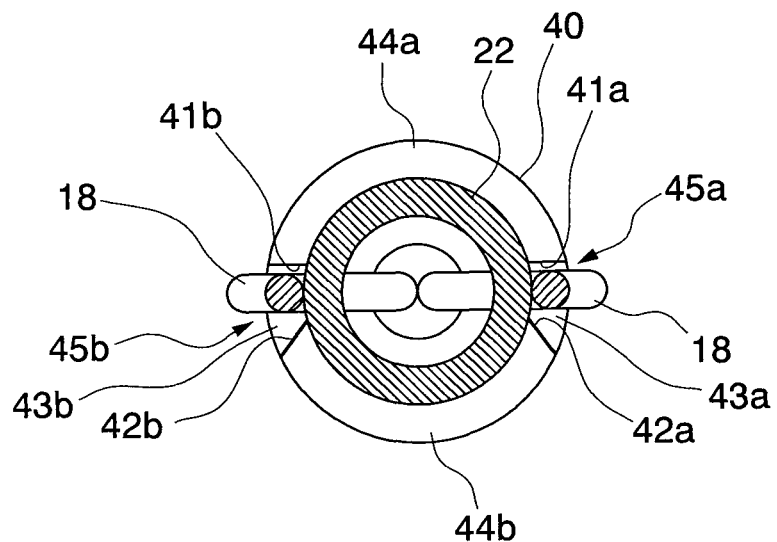
FIG. 11 is a cross-sectional view taken along a line C-C in FIG. 10.

As is shown in FIG. 10 and FIG. 11, V-shaped slits 45a and 45b are provided in a cutting member 40. This cutting member 40 is manufactured with increased strength by performing a heat treatment on a toroidal member that is made from a metal such as stainless steel. The slits 45a and 45b are provided so as to open up towards the distal end, and aperture portions 43a and 43b thereof are formed having a width that is slightly larger than the ligature wire 18. Moreover, one edge of the slit 45a and the slit 45b that is substantially parallel to the axial direction respectively forms a guide surface 41a and a guide surface 41b. Cutting blades 42a and 42b which are inclined blade portions are provided respectively on the other edges (i.e., ridge portions) of the slits 45a and 45b.

Figure 12:
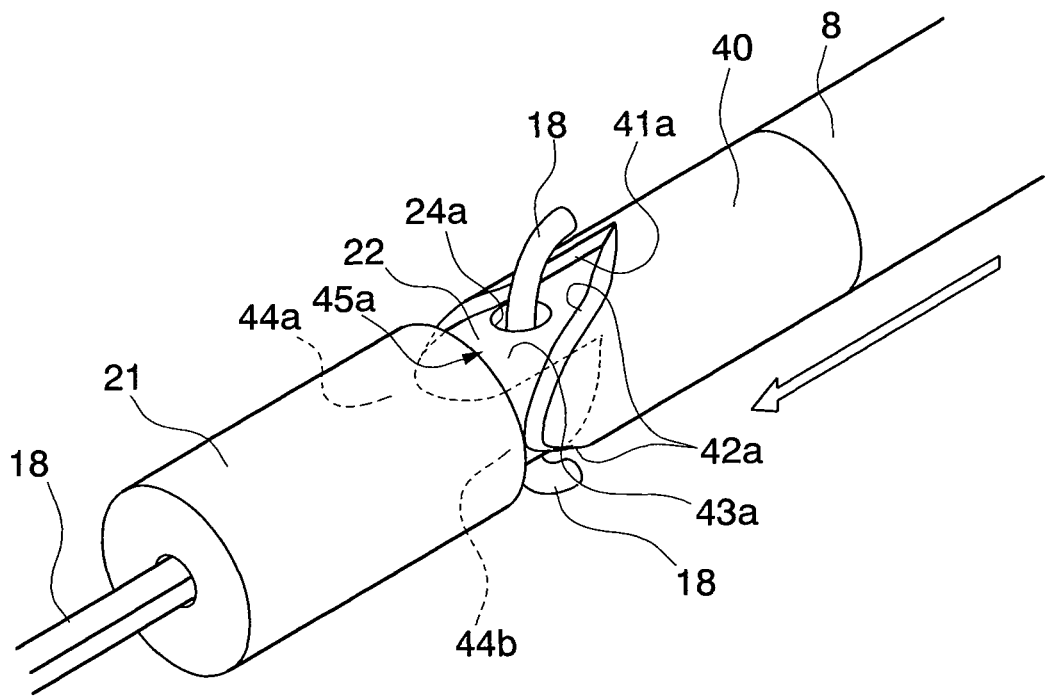
FIG. 12 is a view illustrating movement during a cutting of a ligature wire.

Furthermore, as is shown in FIG. 12, between the slits 45a and 45b, distal end portions 44a and 44b extend in the circumferential direction of the cutting member 40 to the distal end side beyond aperture portions 43a and 43b of the respective slits 45a and 45b. These distal end portions 44a and 44b have rounded distal ends. An angle of inclination θ of the cutting blades 42a and 42b relative to the axial direction is an acute angle, and is desirably between, for example, 5° and 15°. The angle of inclination θ, the position of the base end side holes 25a and 25b, and the length of the slits 45a and 45b are set such that, in a state in which the distal end portions 44a and 44b are abutting against the stopper 21, the cutting blades 42a and 42b extend beyond the base end side holes 25a and 25b but do not extend as far as the distal end side holes 24a and 24b. Because of this, the cutting blades 42a and 42b only cut the exposed portion of the ligature wire 18 once.

An operation of this embodiment will now be described. Note that the operation is the same as in the first embodiment up until the ligaturing step using the ligature wire 18.

If, while the slider 12 is being held, the cutting operation section 13 is operated so that the cutting sheath 8 is moved forward, the cutting sheath 8 moves forward while being guided by the inner sheath 7 and the cutting member 40 slides along while being gently engaged with the base end side of the wire holding member 22. In conjunction with this forward movement of the cutting member 40, the ligature wire 18 enters into the slits 45a and 45b through the aperture portions 43a and 43b of the slits 45a and 45b. It is then guided by the guide surfaces 41a and 41b so as to come up against the cutting blades 42a and 42b and is completely cut. The cutting member 40 stops when the distal end portions 44a and 44b abut against the stopper 21.

Here, because the distal end portions of 44a and 44b of the cutting member 40 have a rounded shape, even if the ligature wire 18 is offset in the circumferential direction from the aperture positions of the slits 45a and 45b, the ligature wire 18 is not damaged by the distal end portions 44a and 44b. Moreover, in cases such as this, the ligature wire 18 is guided by the rounded shapes and is led to the aperture portions 43a and 43b. Accordingly, as is shown in FIG. 12, the ligature wire 18 that is exposed from the wire holding member 22 is cut in the vicinity of the base end side holes 25a and 25b.

According to this embodiment, because it is possible to reliably guide the ligature wire 18 to the cutting blades 42a and 43b without providing the pin and guide groove, the ligature wire 18 can be easily and reliably cut at the blade angle β. Accordingly, manufacturing is made easier and manufacturing costs can be decreased. The remaining effects are the same as those of the first embodiment. Here, the rounded end surfaces of the distal end portions 44a and 44b together with the guide surfaces 41a and 41b function as guide surfaces for guiding the ligature wire 18.

Figure 13:
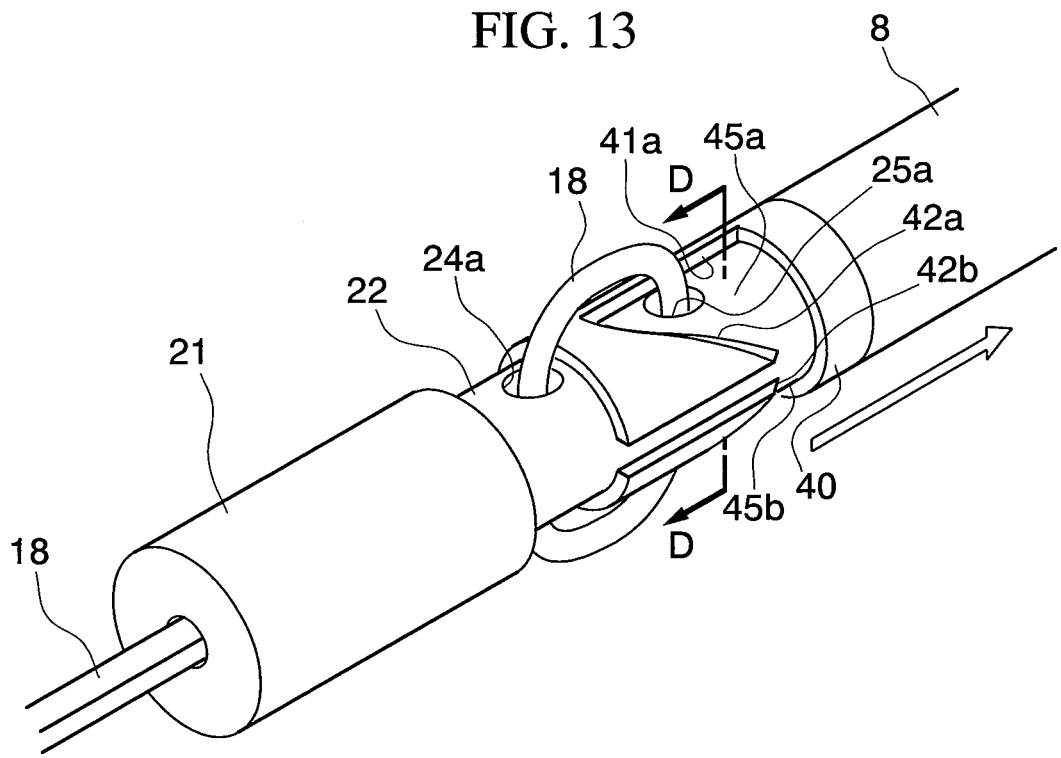
FIG. 13 is a view showing a structure for pulling and cutting a ligature wire.
Figure 14:
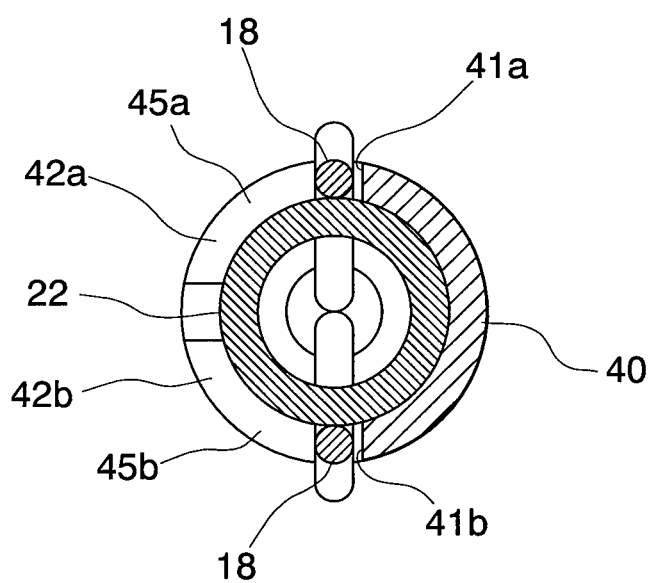
FIG. 14 is a cross-sectional view taken along a line D-D in FIG. 13.

Note that, as is shown in FIG. 13 and FIG. 14, it is also possible for the slits 45a and 45b to be provided so as to open up towards the base end side (i.e., the cutting sheath 8), and for the base end side holes 25a and 25b of the wire holding member 22 to be positioned so as to match the slits 45a and 45b. In this case, by performing an operation such that a cutting operation section 13 such as that shown in FIG. 1 is pulled back towards the finger ring 14 side, the ligature wire 18 can be pulled right back and cut.

(Third Embodiment)

A third embodiment of the present invention will now be described in detail with reference made to FIG. 15 through FIG. 19. This embodiment has the feature that the structure of the cutting member is different from that of the second embodiment. Accordingly, the same symbols are used for member elements that are the same as those in the first embodiment, and any repeated description thereof is omitted.

Figure 15:
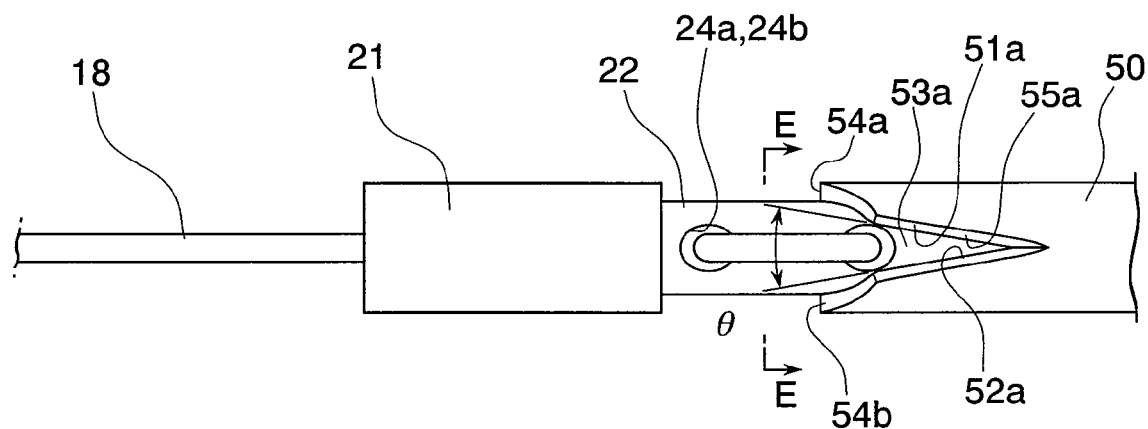
FIG. 15 is a view showing cutting blades provided on both sides of a V shape.
Figure 16:
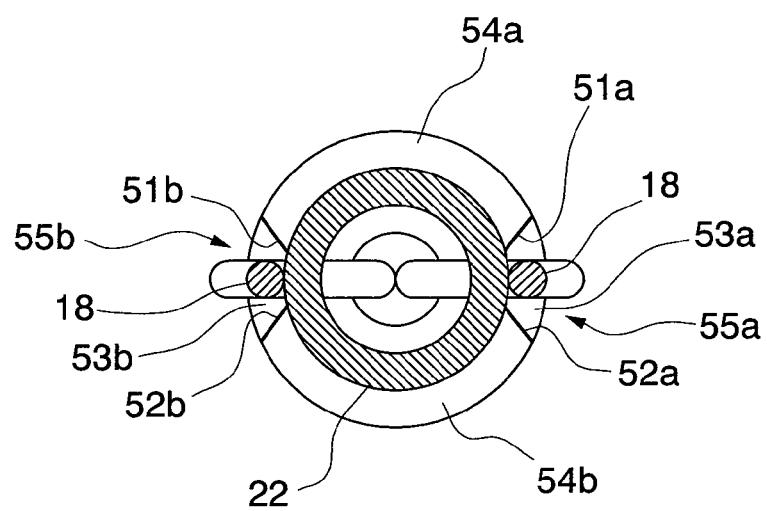
FIG. 16 is a cross-sectional view taken along a line E-E in FIG. 15.

As is shown in FIG. 15 and FIG. 16, a cutting member 50 has a pair of V-shaped slits 55a and 55b, and the two opposing edges thereof form cutting blades 51a and 52a (i.e., first blade portions) and cutting blades 51b and 52b (i.e., second blade portions). The cutting blades 51a and 51b have a symmetrical shape centering on a straight line that is parallel to the axis, and are inclined so as to move apart from each other as they approach aperture portions 53a and 53b on one end side of the distal end, while moving towards each other on the other end side. An angle of inclination θ of the respective cutting blades 51a, 51b, 52a and 52b relative to the axial direction is an acute angle, and is desirably between, for example, 10° and 30°.

Moreover, distal end portions 54a and 54b between the slit 55a and the slit 55b in the circumferential direction of the cutting member 50 protrude beyond the aperture portions 53a and 53b.

Figure 17:
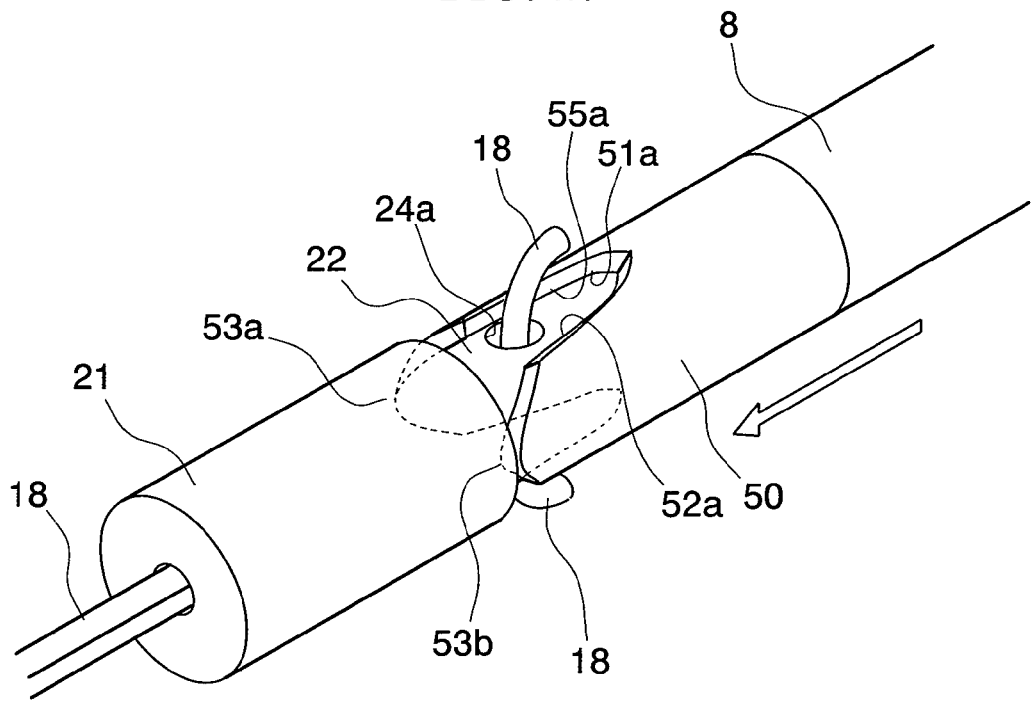
FIG. 17 is a view illustrating movement during a cutting of a ligature wire.

When cutting the ligature wire 18, the ligature wire 18 is pulled into the slits 55a and 55b in conjunction with the movement of the cutting member 50, and moves to the base end side while being cut so as to be sandwiched between the pair of opposing cutting blades 51a, 51b, 52a, and 52b. As a result, the ligature wire 18 is cut perfectly. The cutting member 50 stops when the distal end portions 53a and 53b abut against the stopper 21. Accordingly, as is shown in FIG. 17, the base end portion side of the ligature wire 18 which is inserted in the wire holding member 22 is cut in the vicinity of the base end side holes 25a and 25b. In contrast, the ligature wire 18 is not cut on the distal end side holes 24a and 24b side thereof.

According to this embodiment, by positioning the two cutting blades 51a and 51b as well as 52a and 52b, which are each provided with an angle of inclination, so as to form opposing pairs, the ligature wire 18 is cut so as to be sandwiched from both ends by the pair of opposing cutting blades 51a, 51b, 52a, and 52b. Accordingly, the ligature wire 18 can be cut even more reliably. The remaining effects are the same as in the first embodiment.

Figure 18:
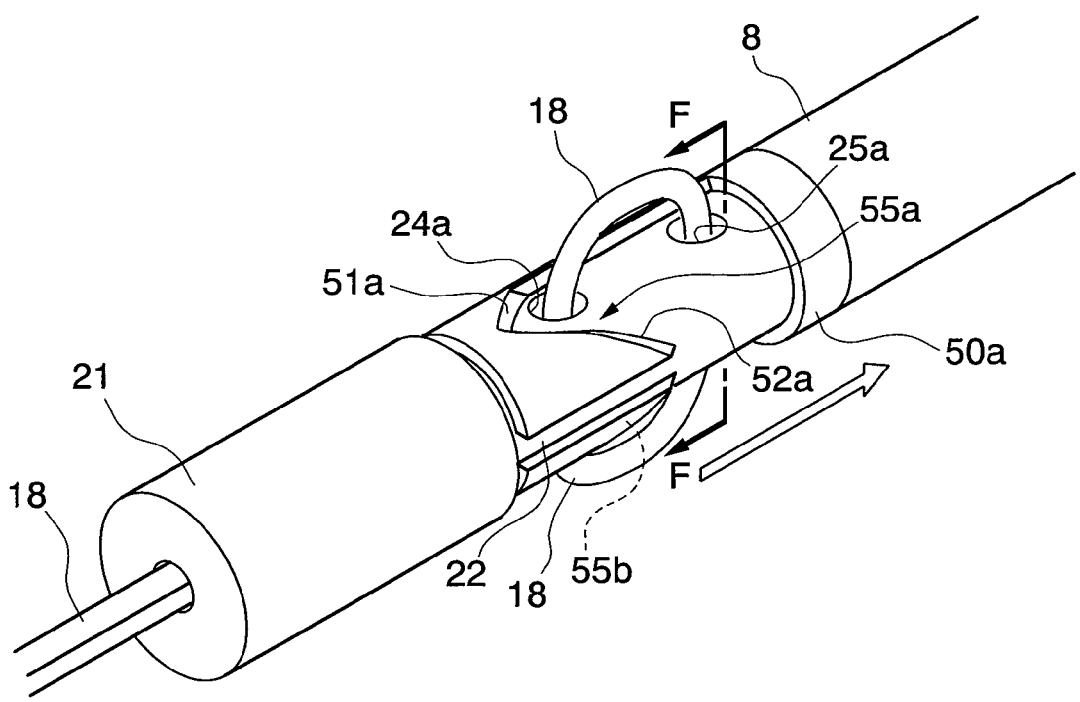
FIG. 18 is a view showing a structure for pulling and cutting a ligature wire.
Figure 19:
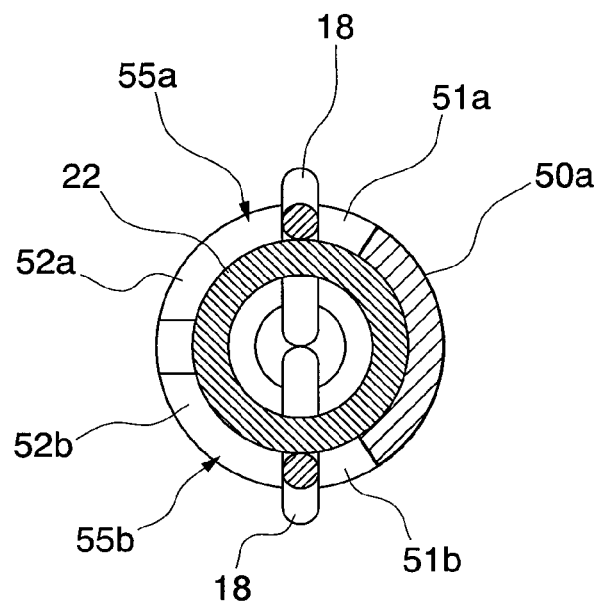
FIG. 19 is a cross-sectional view taken along a line F-F in FIG. 18.

Note that, as in the case of a cutting member 50a shown in FIG. 18 and FIG. 19, it is also possible to employ a structure in which the slits 55a and 55b and the cutting blades 51a, 51b, 52a, and 52b are provided such that they open from the distal end side of the distal end side holes 24a and 24b towards the base end, so that the ligature wire 18 is pulled right back. In this case, the ligature wire 18 is cut in the vicinity of the distal end side holes 24a and 24b. After the ligature wire 18 has been cut, the wire holding member 22 can be easily removed from the cut end portion of the ligature wire 18.

(Fourth Embodiment)

A fourth embodiment of the present invention will now be described in detail with reference made to FIG. 20. In this embodiment, the position of the pair of slits is different from the third embodiment. Accordingly, the same symbols are used for member elements that are the same as those in the above embodiments, and any repeated description thereof is omitted.

Figure 20:
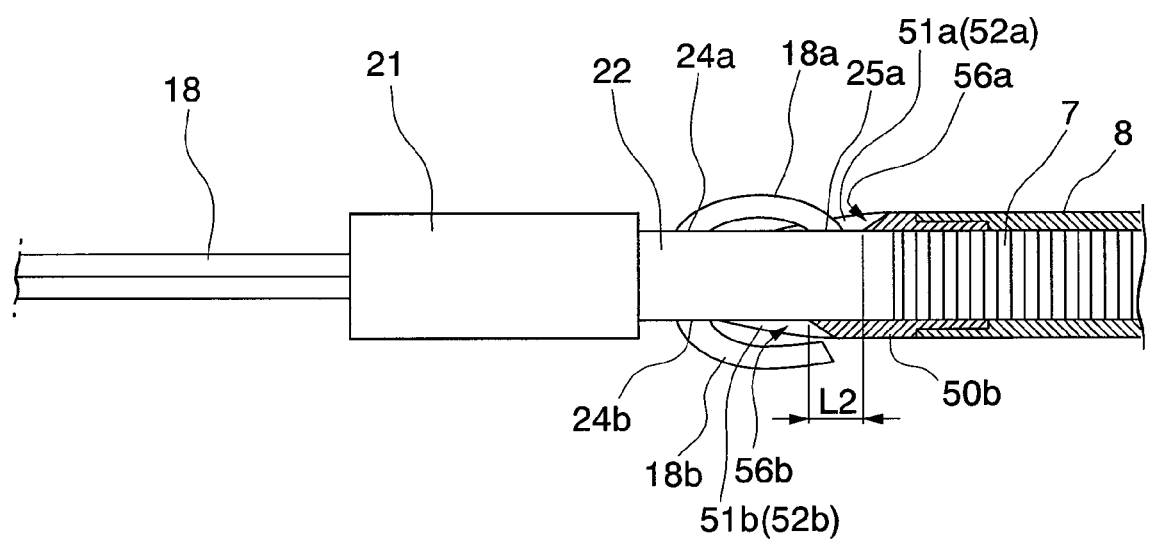
FIG. 20 is a cross-sectional view showing a case in which cutting blades are provided to the front and back.

As is shown in FIG. 20, a cutting member 50b is provided with a cutting portion 56a that is formed by a pair of cutting blades 51a and 51b, and a cutting portion 56b that is formed by a pair of cutting blades 52a and 52b. The cutting portion 56a is provided at a distance L2 on the base end side in the axial direction from the cutting portion 56b. Here, the distance L2 is desirably 0.6 mm or more.

When the ligature wire 18 is being cut, after the exposed portion 18b of the ligature wire 18 has first been cut in conjunction with the forward movement of the cutting member 50b by the cutting portion 56b which is on the distal end side, the cutting portion 56a which is on the base end side cuts the other exposed portion 18a of the ligature wire 18, and the distal end portions 53a and 53b (see FIG. 17) then abut against the stopper 21.

According to this embodiment, by shifting the positions of the cutting blades 51a, 51b, 52a, and 52b forwards or backwards in the forwards and backwards direction, there is absolutely no contact between the two exposed portions 18a and 18b of the ligature wire 18. As a result, there is no dispersion of the cutting force that is applied to the ligature wire 18. Accordingly, the cutting force can be easily concentrated thereby simplifying the cutting of the ligature wire 18.

(Fifth Embodiment)

A fifth embodiment of the present invention will now be described in detail with reference made to FIG. 21 through FIG. 25. Note that the same symbols are used for member elements that are the same as those in the above embodiments, and any repeated description thereof is omitted.

This embodiment differs from the first embodiment in that the cutting sheath is rotatable.

Figure 21:
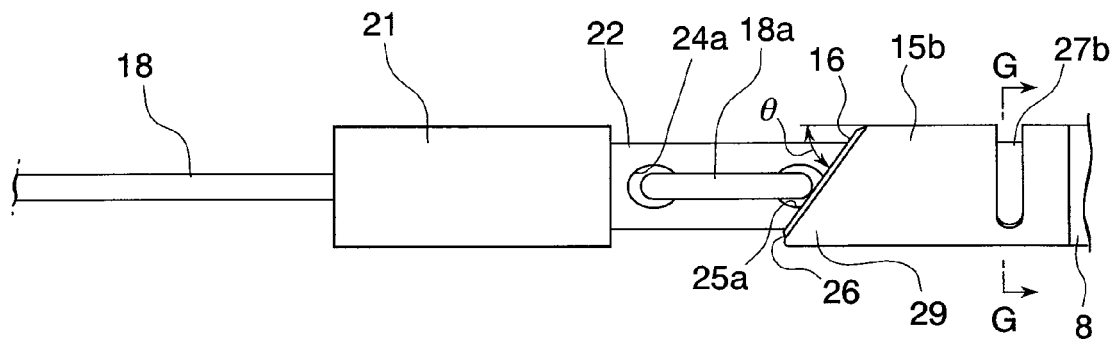
FIG. 21 is a view showing a slit that is provided so as to extend in a circumferential direction of a cutting member.
Figure 22:
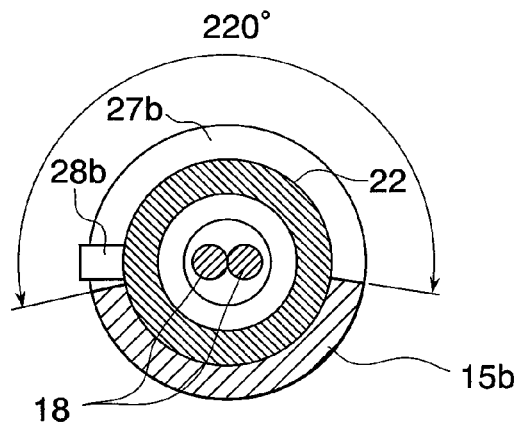
FIG. 22 is a cross-sectional view taken along a line G-G in FIG. 18.

As is shown in FIG. 21 and FIG. 22, the cutting sheath 8 is manufactured from a tube which has excellent rotation followability and which is formed by inserting a metal mesh in flexible plastic such as PTFE. Alternatively, the cutting sheath 8 may be manufactured from a metal coil which has excellent rotation followability.

The cutting blade 16 of the cutting member 15b is provided at a position in the circumferential direction that matches the base end side holes 25a and 25b, and a distal end portion thereof is formed so as not to come into contact with the distal end side holes 24a and 24b even if the cutting member 15b is rotated. Moreover, an inclined end portion 29 which is inclined relative to the axis is formed on a distal end side of the cutting member 15b, and an angle of inclination θ of the inclined end portion 29 is desirably between 75° and 85° relative to the axis. Furthermore, as is shown in FIG. 21, a guide groove 27b is formed in the cutting member 15b as a groove portion that extends in the circumferential direction. A guide pin 28b that has a slightly smaller diameter than the width of the guide groove 27b and that is able to slide smoothly inside the guide groove 27b is provided on the inner sheath 7, so that movement of the cutting member 15b is restricted and only movement in a rotation direction is allowed. Note that, as is shown in FIG. 22, the guide groove 27b extends for not less than 2200 in the circumferential direction.

Next, the operation to cut the ligature wire 18 will be described.

Figure 23:
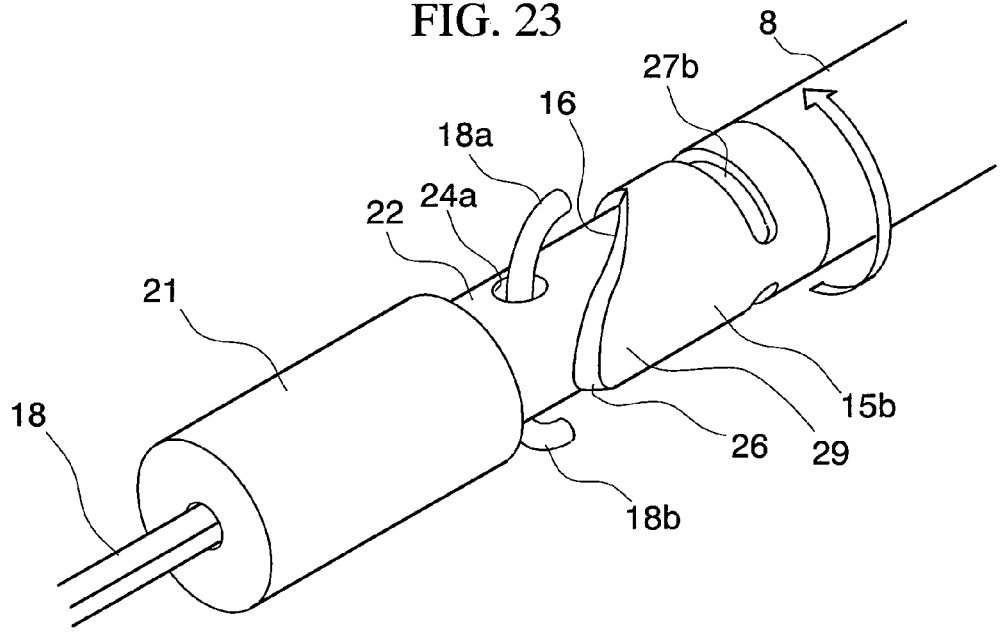
FIG. 23 is a view illustrating movement during a cutting of a ligature wire.

While the slider 12 is being held, the cutting operation section 13 is operated so that the cutting sheath 8 is rotated. As is shown in FIG. 23, the cutting sheath 8 rotates while being guided by the guide pin 28b of the inner sheath 7 (see FIG. 1), and the cutting blade 16 that is formed on the inclined end portion 29 of the cutting member 15 firstly cuts the exposed portion 18a of the ligature wire 18 which is exposed from the base end side hole 25a. Furthermore, because the cutting blade 16 is pressed against the exposed portion 18b of the ligature wire 18 as the cutting member 15 is rotated, this exposed portion 18b is cut next.

According to this embodiment, because the exposed portion 18a of the ligature wire 18 and the exposed portion 18b of the ligature wire 18 are pressed in sequence against the cutting blade 16 as a result of the rotation of the cutting member 15, there is no dispersion of the force required for the cutting. Accordingly, the ligature wire 18 can be reliably cut. Moreover, because there is no need to move the cutting member 15 forwards and backwards, even if the outer diameter of the stopper 21 is smaller than the wire holding member 22 of the cutting member 15, the cutting member 15 does not stick out on the distal end side beyond the distal end of the wire holding member 22 and damage the stopper 21. The remaining effects are the same as in the first embodiment.

Figure 24:
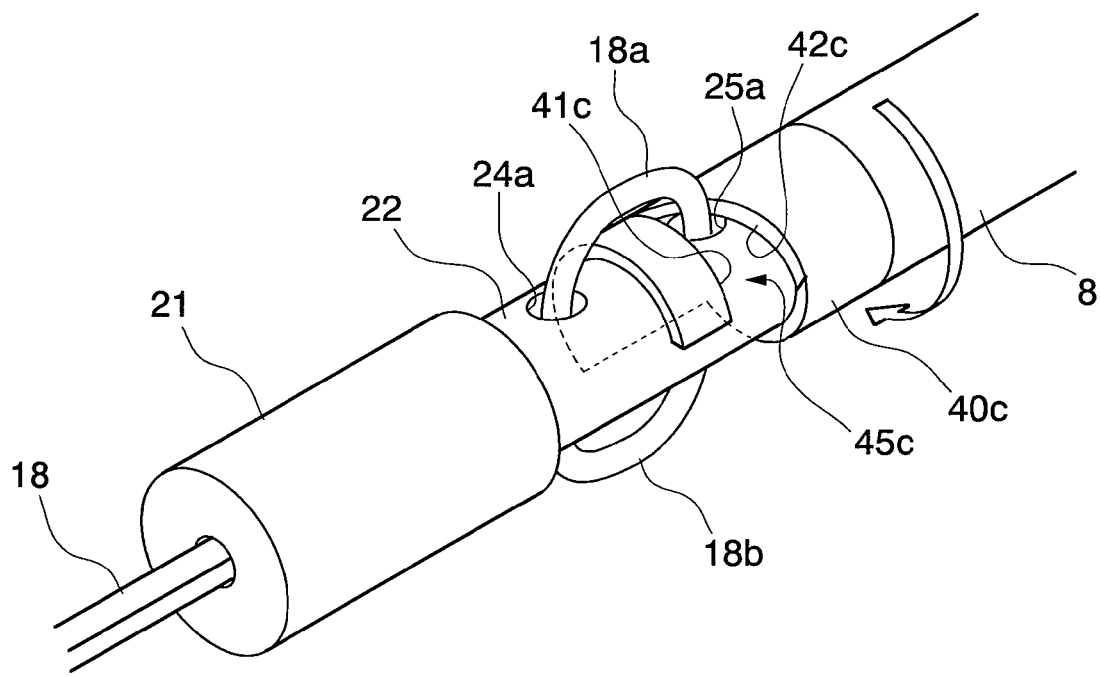
FIG. 24 is a view showing a cutting blade provided in a circumferential direction.

Note that, as in the case of a cutting member 40c shown in FIG. 24, it is also possible to provide a V-shaped slit 45c that extends in the circumferential direction. In this case, a guide surface 41c and a cutting blade 42c of the cutting member 40c are provided at a predetermined angle of inclination relative to the circumferential direction. If the cutting operation section 13 is rotated such that the cutting blade 42c is pressed against the exposed portion 18a of the ligature wire 18, then this exposed portion 18a is cut first, and if the cutting member 40c is then rotated further, the exposed portion 18b of the ligature wire 18 is cut next.

Figure 25:
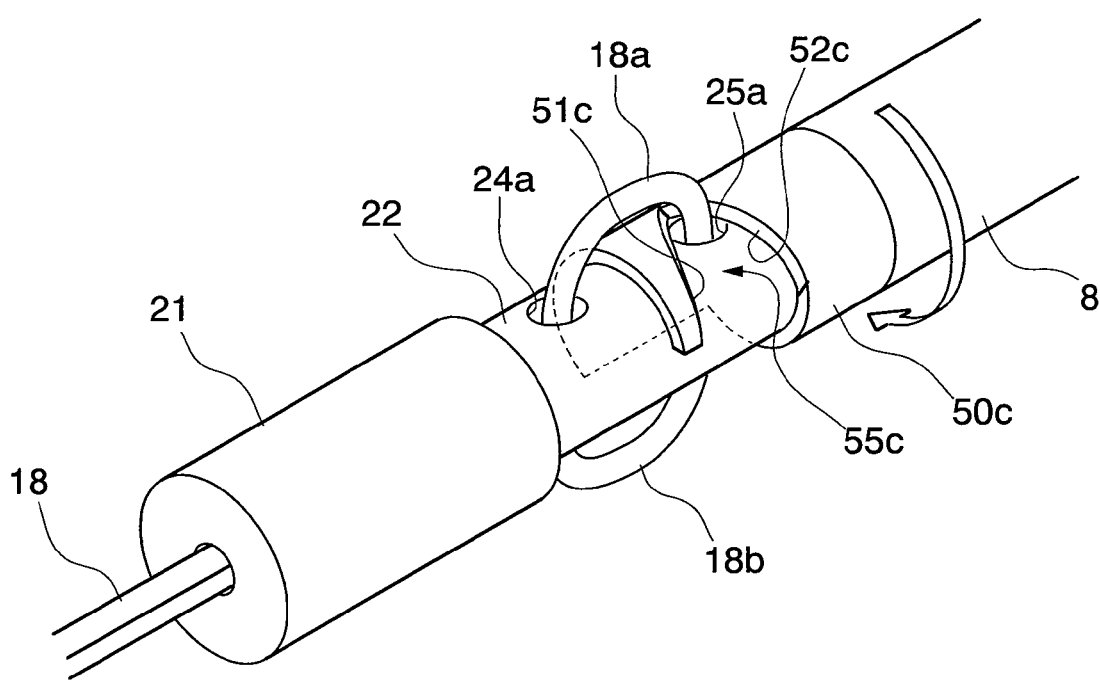
FIG. 25 is a view showing cutting blades provided on both sides of a V shape that opens up in the circumferential direction.

Moreover, as in the case of a cutting member 50c shown in FIG. 25, it is also possible to provide a V-shaped slit 55c that extends in the circumferential direction. In this case, a pair of cutting blades 51c and 52c of the cutting member 50c are provided so as to approach each other at one end side thereof and move away from each other at the other end side thereof. If the cutting operation section 13 is rotated such that the cutting blades 51c and 52c are pressed against the exposed portion 18a of the ligature wire 18, then this exposed portion 18a of the ligature wire 18 is cut first, and if the cutting member 50c is then rotated further, the exposed portion 18b of the ligature wire 18 is cut next.

(Sixth Embodiment)

A sixth embodiment of the present invention will now be described in detail with reference made to FIG. 26 through FIG. 30. Note that the same symbols are used for member elements that are the same as those in the above embodiments, and any repeated description thereof is omitted.

Figure 26:
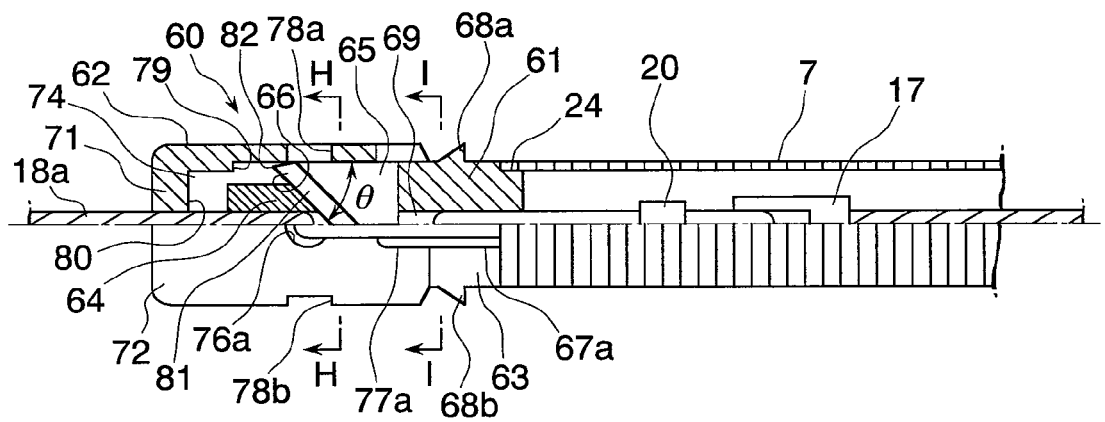
FIG. 26 is a partial cross-sectional view showing the structure of a wire holding member and a cutting member.
Figure 27:
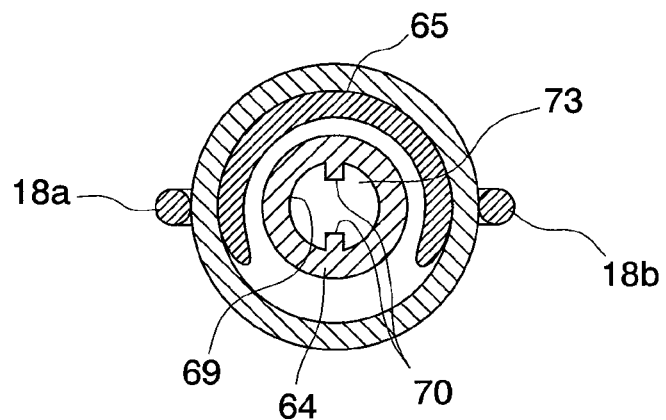
FIG. 27 is a cross-sectional view taken along a line H-H in FIG. 26.
Figure 28:
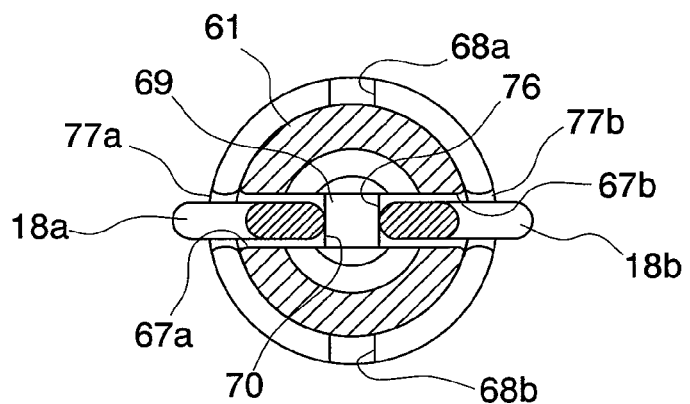
FIG. 28 is a cross-sectional view taken along a line I-I in FIG. 26.
Figure 29:
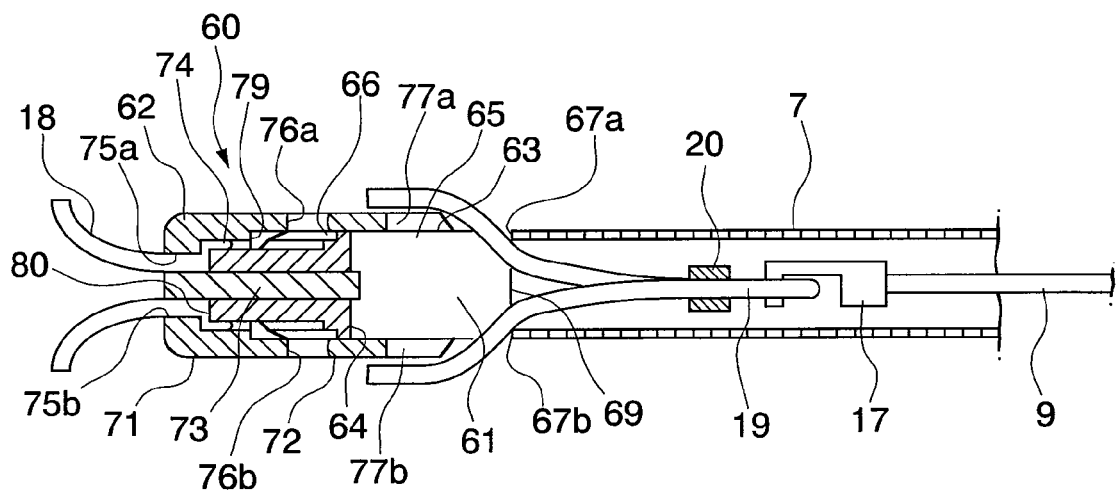
FIG. 29 is a view illustrating movement during a cutting of a ligature wire.

As is shown in FIG. 26 through FIG. 28, a fixing member 60 is provided on the distal end side of the inner sheath 7. This fixing member 60 is preferably formed from a material that is comparatively rigid while having excellent flowability such as a plastic such as polypropylene, ABS, polyacetal, or polycarbonate, or a liquid polymer or polyphthalamide, however, it may also be formed from a metal such as stainless steel or aluminum. The outer diameter of the fixing member 60 is approximately (φ1 to 3 mm, while the length thereof is approximately 5 to 10 mm.

The fixing member 60 is constituted by a first member 61 and a second member 62. The first member 61 is a circular cylinder, and a large diameter portion 63 is provided at a base end portion thereof which is connected to the inner sheath 7, while a press-insertion portion 64 which is a small diameter portion is provided at a distal end portion thereof. Furthermore, a toroidal cutting member 65 is fitted onto an outer circumference at the distal end side of the large diameter portion 63. This cutting member 65 is formed from a metal such as stainless steel, and has had its hardness increased as a result of undergoing a heat treatment. A sharpened cutting blade 66 that faces towards the distal end is formed on an inclined end portion 81 which is inclined relative to the axis. This cutting blade 66 has an angle of inclination θ relative to the axial direction. The angle of inclination θ is an acute angle, and is desirably between 5° and 15°. Furthermore, slit-shaped wire guides 67a and 67b are provided in an outer circumference on the base end side of the fixing member 60. Engaging claws 68a and 68b are provided so as to protrude outwards at positions offset by 90° in the circumferential direction from the wire guides 67a and 67b. Moreover, an inner cavity 69 that extends along the axis is provided in a shaft portion of the first member 61, and projections 70 are provided in substantially an intermediate portion in the axial direction of the inner cavity 69. A suitable height for these projections 70 is between 0.1 and 0.3 mm.

As is shown in FIG. 26, the second member 62 has a portion 71 having the shape of a circular column at the distal end portion thereof, and a fixing inner cavity 74 is provided extending towards the base end side in this columnar portion 71. A suitable length for the fixing inner cavity 74 is between 1 and 3 mm. Moreover, an insertion shaft 73 is provided in the center of the columnar portion 71 so as to protrude through the fixing inner cavity 74 to the base end side and be inserted into the inner cavity 69 of the first member 61. Furthermore, distal end holes 75a and 75b through each of which respectively one ligature wire 18 is inserted are provided in a distal end portion of the second member 62 so as to avoid the insertion shaft 73. An abutment portion 80 of the press-insertion portion 64 is provided in the vicinity of the distal end portion of the fixing inner cavity 74. In addition, the clearance on one side between the inner diameter of the fixing inner cavity 74 and the outer diameter of the press-insertion portion 64 is set so as to be smaller than the outer diameter of the ligature wire 18.

A cylindrical portion 72 is provided integrally with the columnar portion 71 from the base end portion of the columnar portion 71. Side holes 76a and 76b are provided in an outer circumference of the cylindrical portion 72 of the second member 62, and slits 77a and 77b are provided respectively on the base end side of these side holes 76a and 76b. Furthermore, two engaging holes 78a and 78b are provided in the cylindrical portion 72 at positions that are offset 90° in the circumferential direction from the slits 77a and 77b so as to be able to engage with the engaging claws 48a and 48b of the first member 41.

The positions in the axial direction of the side holes 78a and 78b are set such that, when the distal end portion of the cutting member 65 is abutting against an abutment surface 79 of the columnar portions 71, these side holes 78a and 78b are closed off by the inclined end portion 81 of the cutting members 65. Moreover, the abutment surface 79 of the cutting blade 66 is provided on an inner circumferential portion of the columnar portion 71 of the second member 62.

The insertion shaft 73 of the second member 62 is inserted into the inner cavity 69 of the first member 61, and a distal end surface of the insertion shaft 73 abuts against the projections 70 thereby restricting the insertion depth. Accordingly, the cylindrical portion 72 of the second member 62 is fitted onto an outer circumferential portion of the cutting member 65 and is placed in a state in which it covers the cutting blade 66. The ligature wire 18 is inserted through the distal end holes 75a and 75b into the interior of the second member 62, and is guided to the outside through the side holes 76a and 76b. The ligature wire 18 is then guided by the slits 77a and 77b and the wire guides 67a and 67b to the base end side of the fixing member 60. The bond between the folded back portion 19 of the ligature wire 18 and the double-ended connecting pipe 20 is the same as in the first embodiment.

When the ligature wire 18 is being cut, the operating wire 9 is moved forward and the engaging member 17 is made to protrude from the distal end aperture of the inner sheath 7. In this state, the folded back portion 19 of the base end portion of the ligature wire 18 is made to catch onto the hook portion of the engaging member 17. When the operating wire 9 is moved backward and the engaging member 17 is pulled back inside the inner sheath 7, the fixing member 60 is supported in the inner sheath 7. In this state, the inner sheath 7 including the ligature wire 18 is inserted into the channel of an endoscope and this endoscope is then inserted into a body cavity. The distal end portion of the sheath 7 is then guided to the target position inside the body cavity. While a lesion portion W such as a polyp or the like is being monitored using the endoscope, if the inner sheath 7 is moved forwards, the ligature wire 18 is made to protrude from the distal end aperture of the channel, and the loop portion of the ligature wire 18 is elastically restored and the diameter thereof is enlarged.

Next, after the loop portion of the ligature wire 18 has been placed around the base of the lesion portion W as the lesion portion W is being monitored using the endoscope, the operating wire 9 is moved backwards. The base end portion of the ligature wire 18 is pulled inside the inner sheath 7 via the engaging member 17, and the diameter of the ligature wire 18 is contracted so that the lesion portion W is tightly bound. If the operating wire 9 is then moved further backwards, the distal end surface of the second member 62 of the fixing member 60 comes up against the lesion portion W so that the lesion portion W forms a stopper. As a result, the first member 61 moves forwards relatively and the second member 62 moves backwards relatively. Accordingly, the insertion shaft 73 of the second member 62 surmounts the projections 70, and is inserted into the inner cavity 69 of the first member 61.

Because the press-insertion portion 64 of the first member 61 moves forward towards the fixing inner cavity 74 of the second member 62, an intermediate portion of the ligature wire 18 is fixed in a state of being gripped between an inner surface portion of the fixing inner cavity 74 and an outer circumferential portion of the press-insertion portion 64. Furthermore, after the press-insertion portion 64 of the first member 61 has moved forwards towards the fixing inner cavity 74 of the second member 62 and has been gripped and fixed, when the press-insertion portion 64 of the first member 61 is moved further forward towards the fixing inner cavity 64 of the second member 62, the distal end side of the cutting blade 66 on the inclined surface is pressed against the ligature wire 18, and the ligature wire 18 is cut by the cutting blade 66 as the cutting member 65 moves forward. When a distal end portion 82 of the cutting blade 66 is placed against the abutment surface 79, the base end side of the ligature wire 18 is gripped between the press-insertion portion 64 and the abutment portion 80. Furthermore, the engaging claws 68a and 68b of the first member 61 are engaged in the engaging holes 78a and 78b of the second member 62, so that the first member 61 and the second member 62 are placed in an engaged state. On the other hand, as a result of the ligature wire 18 being cut the inner sheath 7 is separated from the fixing member 60, so that the ligature tool for medical treatment 2 and the operating device 3 are completely separated from each other. When the insertion portion 4 is withdrawn from the channel of the endoscope, only the ligature wire 18 which was being held in a tightly bound state by the fixing member 60 is left behind in the patient and the operation to tightly bind the lesion portion W is ended.

According to this embodiment, the same effects as in the first and third embodiments are obtained.

Figure 30:
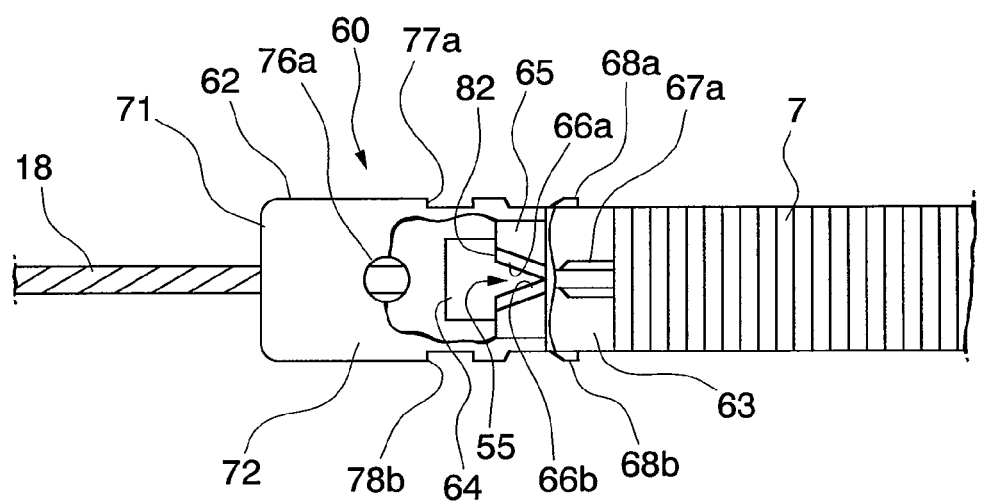
FIG. 30 is a view showing cutting blades provided on both sides of a V shape.

Note that, as is shown in FIG. 30, it is also possible to provide a V-shaped slit 55 that faces towards the distal end and the cutting blades 66a and 66b such as were shown in the third embodiment in the cutting member 65, and to then cut the ligature wire 18.

(Seventh Embodiment)

A seventh embodiment of the present invention will now be described in detail with reference made to FIG. 31 through FIG. 35. Note that the same symbols are used for member elements that are the same as those in the above embodiments, and any repeated description thereof is omitted.

Figure 31:
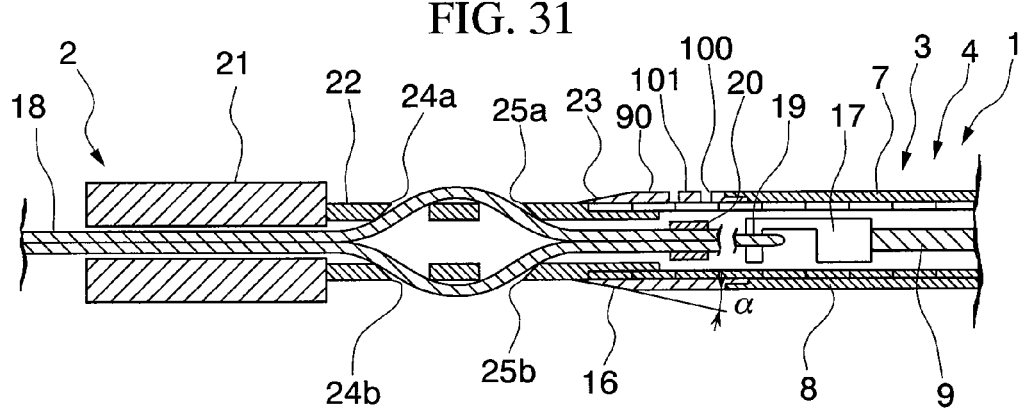
FIG. 31 is a cross-sectional view showing a cutting member that moves in a spiral.
Figure 32:
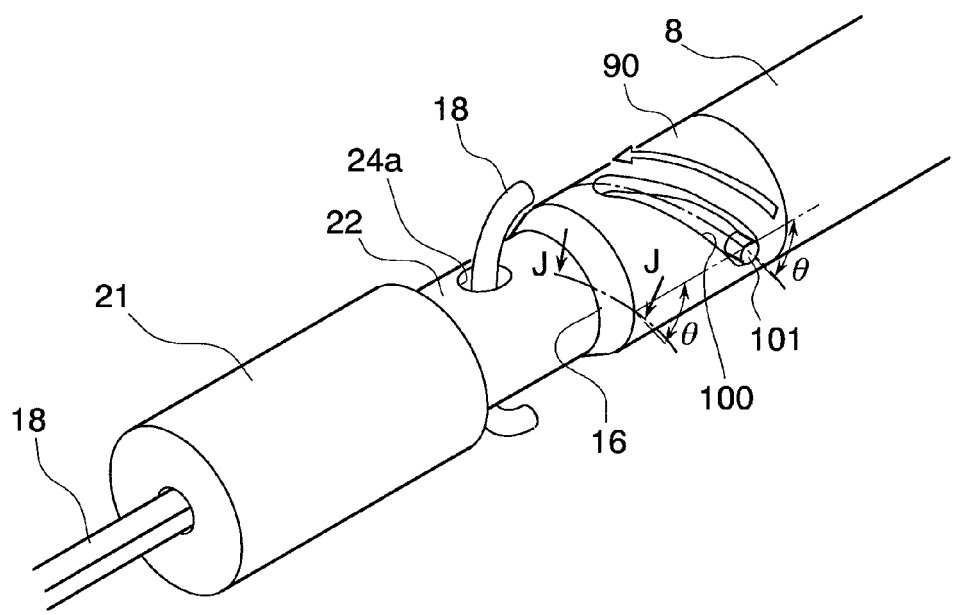
FIG. 32 is a perspective view showing a cutting member that moves in a spiral.
Figure 33:
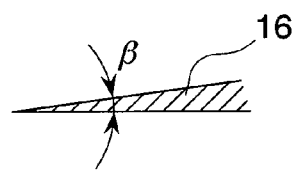
FIG. 33 is a cross-sectional view taken along a line J-J in FIG. 32.

As is shown in FIG. 31 through FIG. 33, a cutting member 90 is provided as a cutting device at a distal end of the cutting sheath 8. The cutting member 90 is formed from a metal such as stainless steel and is a toroidal member whose hardness has been improved as a result of undergoing heat treatment. A distal end portion of the cutting member 90 is substantially at a right angle relative to the longitudinal direction thereof, and a cutting blade 16 that has an acute blade angle α is provided around the entire circumference thereof.

A guide groove 100 that causes the cutting member 90 to rotate in a spiral configuration around its axis is provided in the cutting member 90. The guide groove 100 has an angle of inclination θ relative to its direction of forward and backward movement, and it is desirable for this angle of inclination θ to be between 75° and 85°. A guide pin 101 that protrudes to the outer side in the radial direction is provided on the inner sheath 7. The guide pin 101 has a slightly smaller diameter than the width of the guide groove 100, and is able to slide smoothly inside the guide groove 100. The guide pin 101 restricts the movement of the cutting member 90 during its forwards and backwards movements, and the range of operation in the axial direction of the cutting member 90 when the guide groove 100 and the guide pin 101 are combined together is from the top of the inner sheath 7 to the front of the distal end side holes 24a and 24b of the wire holding member 22.

An operation of this embodiment will now be described. If the cutting operation section 13 is operated while the slider 12 is being held so that the cutting sheath 8 is moved forward or rotated, the cutting member 90 is moved forward in a spiral configuration via the cutting sheath 8 in accordance with the guide groove 100 and the guide pin 101, and engages with the base end portion of the wire holding member 22. The cutting member 90 moves until the guide pin 101 hits the base end side of the guide groove 100. At this time, because the cutting blade 16 that is pressing against the ligature wire 18 is moving in a spiral configuration, as is shown in FIG. 33, the actual angle of the cutting blade 16 becomes the angle β, which is more acute than the blade angle α. Accordingly, by causing the cutting member 90 to move in a spiral configuration, the ligature wire 18 that is exposed from the base end side holes 25a and 25b is cut.

According to this embodiment, it is possible to achieve the same affects as those of the first embodiment without providing a cutting blade 16 which is inclined in the axial direction.

Figure 34:
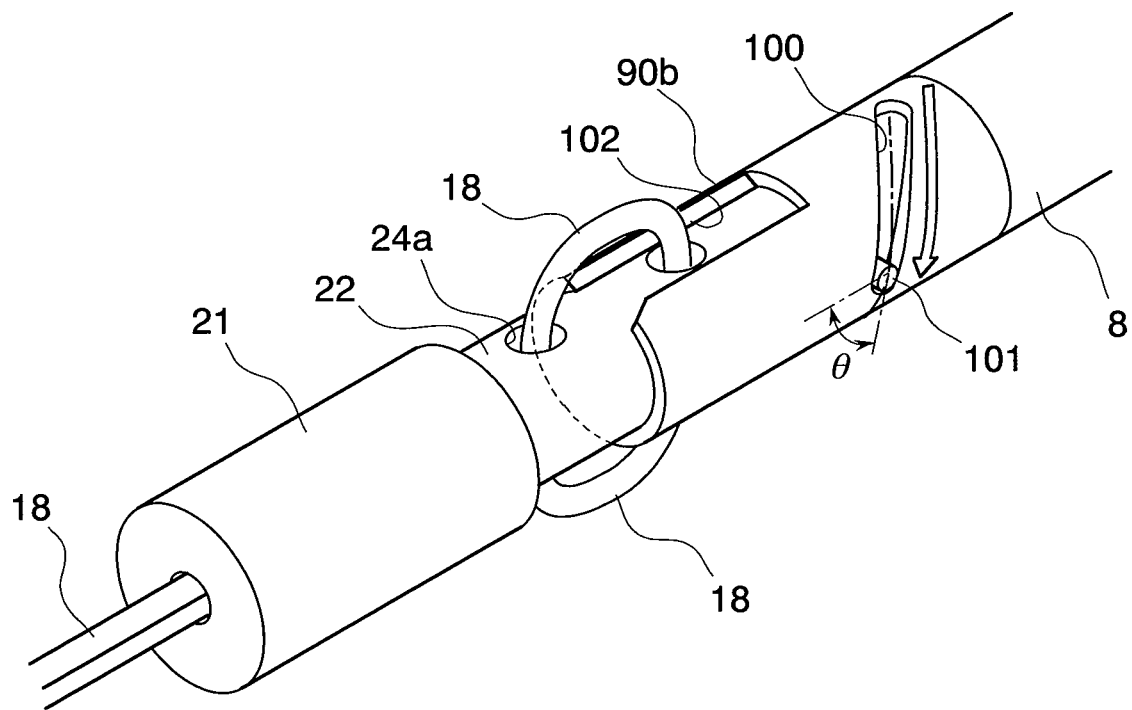
FIG. 34 is a view showing a cutting member that moves in a spiral and in which cutting blades are provided in parallel to the axis.

Note that, as is the case with a cutting member 90b shown in FIG. 34, it is also possible to provide a cutting blade 102 in parallel with the axial direction. In this case, the guide groove 100 which is rotated in a spiral configuration has an angle of inclination θ relative to the axis. The angle of inclination θ is desirably between 5° and 15°.

Figure 35:
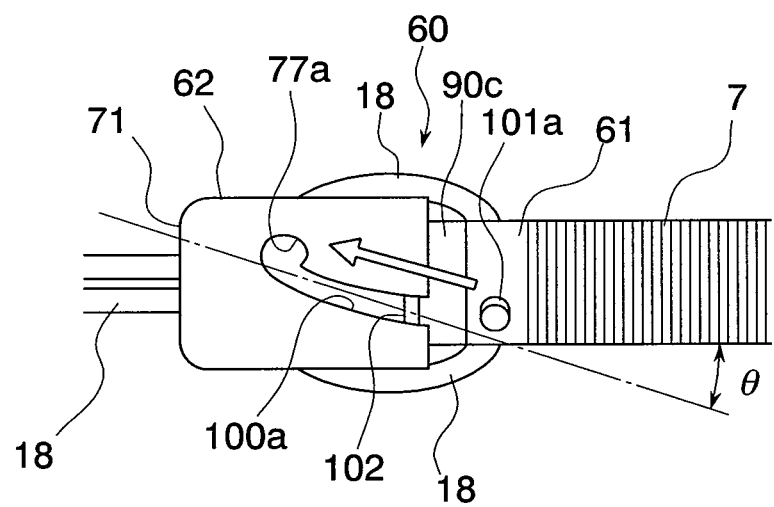
FIG. 35 is a view showing another form of a cutting member that moves in a spiral.

Moreover, as in the case of a cutting member 90c shown in FIG. 35, it is possible to employ a toroidal member in which a sharp cutting blade 102 is formed around the entire circumference of a distal end portion which is substantially at a right angle relative to the axial direction, and to provide a guide pin 101a in the first member 61 of the fixing member 60 and provide a guide groove 100a in the second member 62. The guide groove 100 is formed at an angle of inclination θ relative to the axial direction. This angle of inclination θ is desirably between 10° and 30°.

(Eighth Embodiment)

An eighth embodiment of the present invention will now be described in detail with reference made to FIG. 36 through FIG. 41. Note that the same symbols are used for member elements that are the same as those in the above embodiments, and any repeated description thereof is omitted.

This embodiment relates to a suture device for medical treatment that sutures a lesion portion that is hemorrhaging or the like, and employs a suture thread as the suture member.

Figure 36:
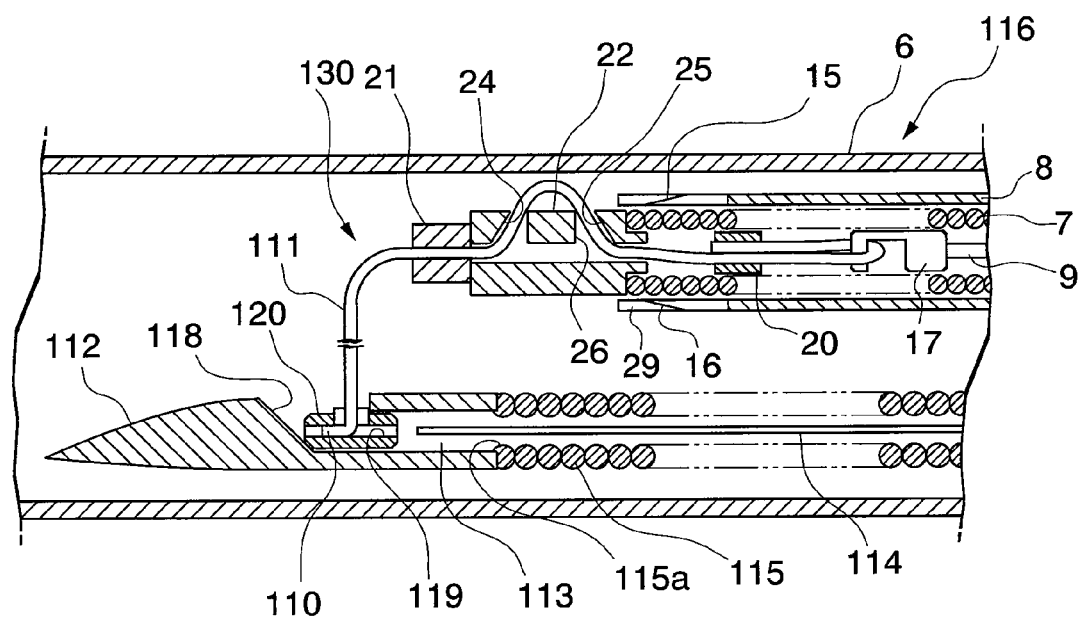
FIG. 36 is an enlarged cross-sectional view of a distal end portion when the distal end portion has a puncturing member.

As is shown in FIG. 36, a suture device for medical treatment 116 which is a suture and ligature device for medical treatment is provided with an anchoring chip 110 that is connected to a distal end of a suture thread 111, and with a suture needle body 115 that houses the anchoring chip 110 such that it can be freely inserted and removed and that has a puncturing member 112 that punctures biological tissue provided at a distal end thereof. The suture needle body 115 is formed in a pipe shape by a tightly wound coil made from a metal such as stainless steel, and has sufficient flexibility to allow it to be bent inside the channel of an endoscope. The puncturing member 112 is mounted on the distal end of the suture needle body 115. The puncturing member 112 is manufactured from a metal material such as stainless steel. A distal end thereof is formed having a sharp elongated configuration and the outer diameter thereof is manufactured at the same size as the suture needle body 115. Moreover, an aperture portion 118 is formed in a side portion of the puncture member 112. A housing portion 113 that is connected to an inner hole 115a of the suture needle body 115 is formed in this aperture portion 118. The anchoring chip 110 of a suture tool for medical treatment 130 which is a suture and ligature tool for medical treatment is housed in this housing portion 113.

The suture tool for medical treatment 130 is formed by the anchoring chip 110, the suture thread 111 which is a flexible wire material, the stopper 21, and the wire holding member 22. Note that the wire holding member 22 that is used has one distal end side hole 24a and one base end side hole 25a.

The anchoring chip 110 is formed in a pipe shape, and the suture thread 111 is inserted through a slit 119 in an intermediate portion thereof. A fixing portion that fixes the suture thread 111 in the anchoring chip 110 is formed by adhesion or by caulking the anchoring chip 110. Moreover, the anchoring chip 110 is housed in the housing portion 113 with the longitudinal direction thereof matching the longitudinal direction of the suture needle body 115. A flexible pushing wire 114 is inserted into an inner cavity of the suture needle body 115 such that it can be moved freely backwards and forwards. The flexible pushing wire 114 serves as a pushing device for pushing out from the housing portion 113 the anchoring chip 110 that is housed in the housing portion 113. This pushing wire 114 can be moved backwards and forwards by the manual operating section 5.

Moreover, in this embodiment, the cutting sheath 8 and the suture needle body 115 are covered by the outer sheath 6. Namely, the suture needle body 115 is formed so as to be able to move freely backwards and forwards inside the outer sheath 6 independently from the cutting sheath 8. Operations of this suture needle body 115 are also performed by the manual operating section 5.

An operation of this embodiment will now be described.

Firstly, after a surgeon has confirmed using endoscope images that the distal end of the endoscope has reached a lesion portion that is to be sutured, as is shown in FIG. 36, the suture device for medical treatment 116 is inserted into the endoscope channel in a state of covering the circumference of the outer sheath 6, the cutting sheath 8, and the suture needle body 115.

Figure 37:
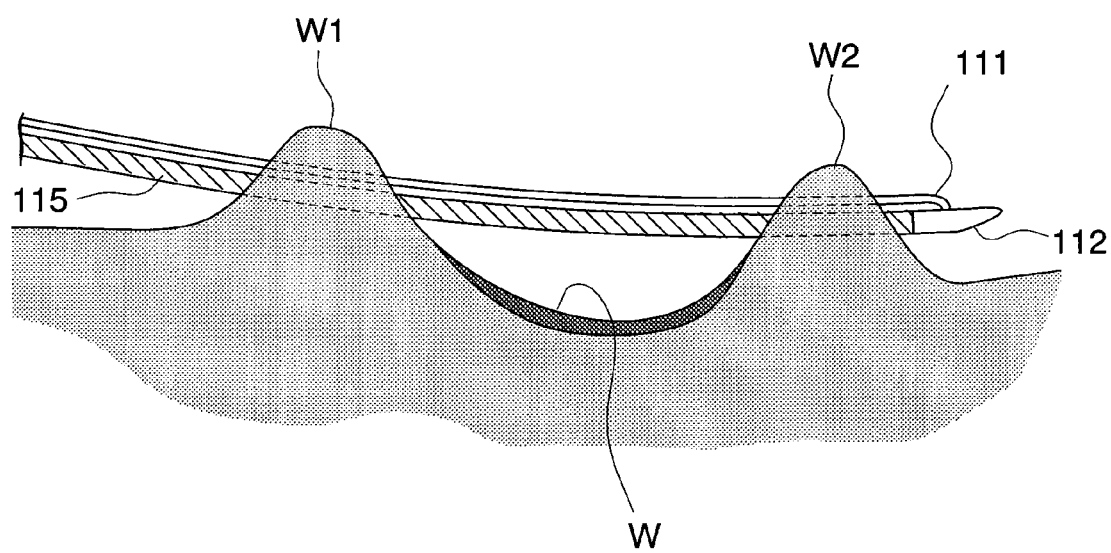
FIG. 37 is a view illustrating a treatment, and shows the puncturing member piercing body tissue.
Figure 38:
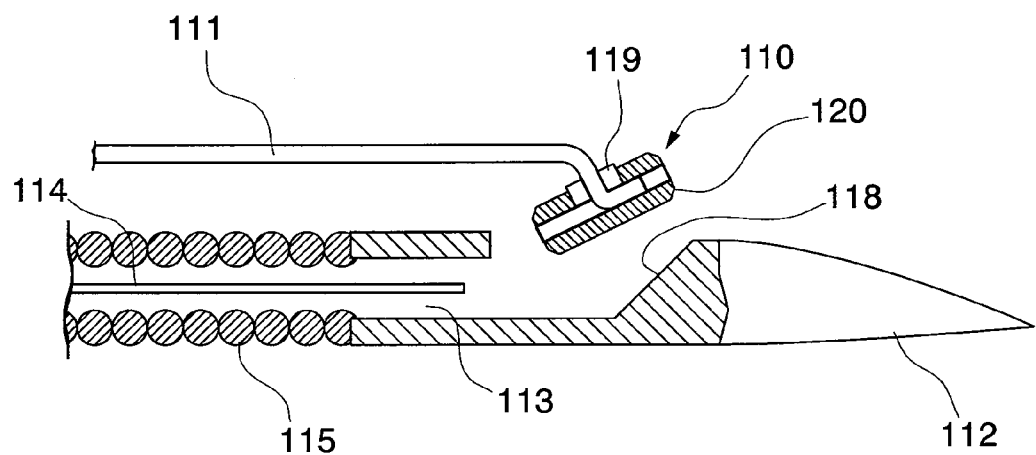
FIG. 38 is a view showing an anchoring member being pushed out from the puncturing member.

Once it has been confirmed that the outer sheath 6 is protruding from the distal end of the endoscope, the outer sheath 6 is moved backwards and the suture needle body 115 is then operated. As is shown in FIG. 37, the puncturing member 112 is made to puncture the tissue W1 in front of the lesion portion W where the hemorrhaging is to be stopped, and the puncturing member 112 is then moved forward to puncture the tissue W2 as well which is on the further side sandwiching the lesion portion W. In this state, as is shown in FIG. 38, the pushing wire 114 is pushed in the direction of the distal end so that the anchoring chip 110 is pushed out from the housing portion 113.

Figure 39:
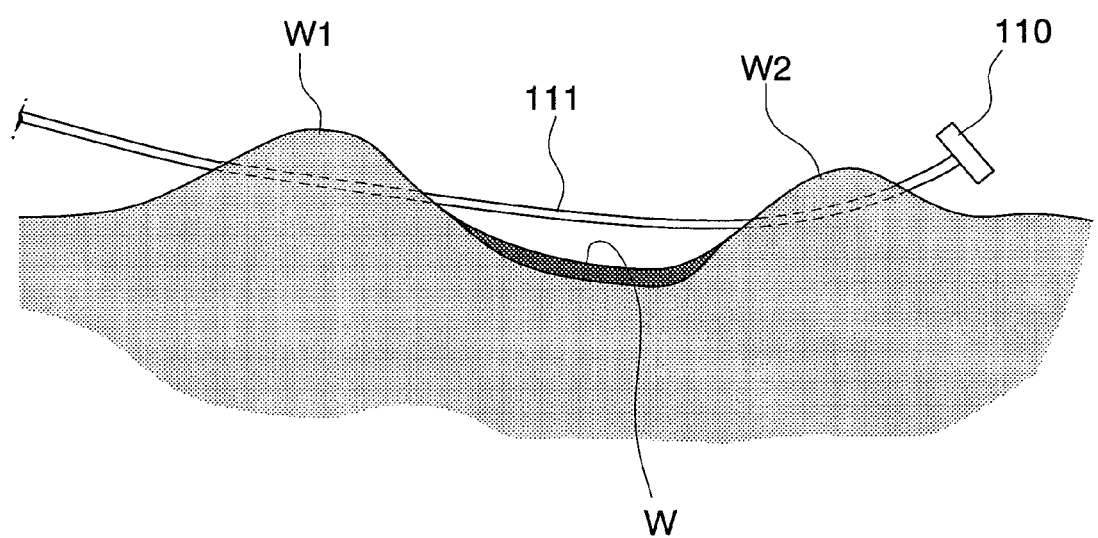
FIG. 39 is a view showing when the puncturing member has been withdrawn from the body tissue.

Because the anchoring chip 110 is in a state of separation from the suture needle body 115, an operation to withdraw the suture needle body 115 is performed after this. As is shown in FIG. 39, the anchoring chip 110 is caught in the tissues W1 and W2, and the suture thread 111 that is fixed in the anchoring chip 110 penetrates the two tissues W1 and W2.

Figure 40:
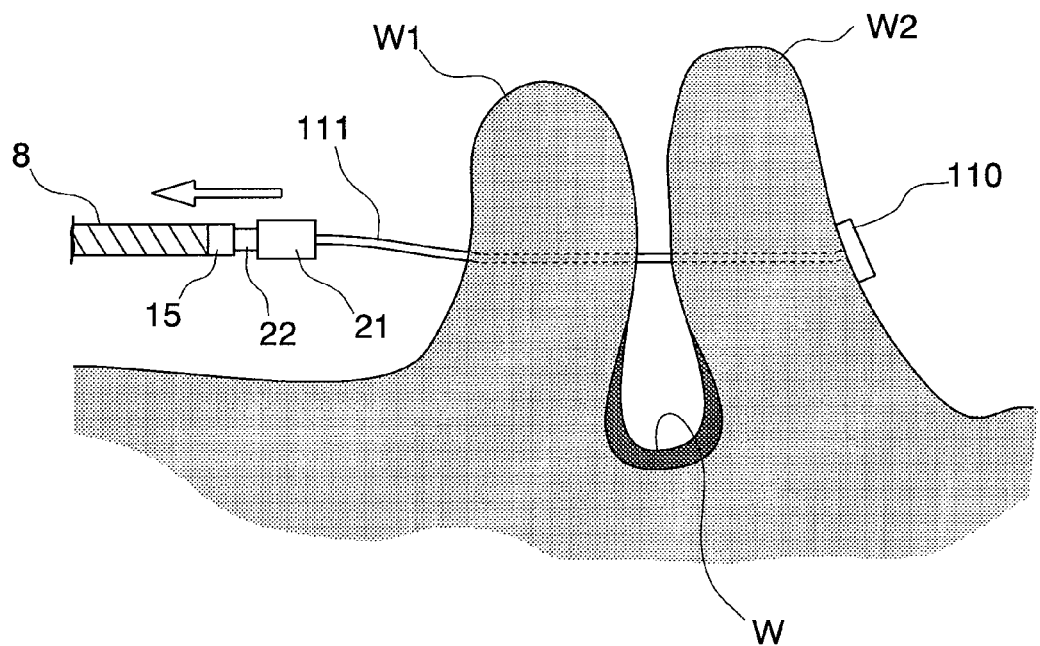
FIG. 40 is a view showing a process for suturing body tissue.
Figure 41:
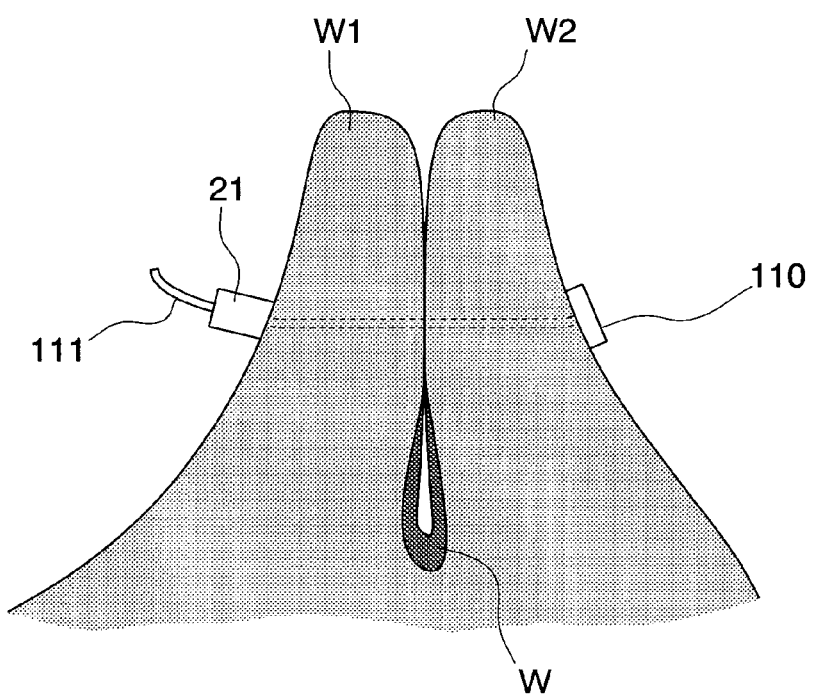
FIG. 41 is a view showing a sutured lesion portion.

Next, in this state the slider 12 is moved towards the base end side and, as is shown in FIG. 40, while the stopper 21 is being pushed out, the tissue is pulled so that the lesion portion W which is the hemorrhaging portion is closed off. If, while the slider 12 is being held, the cutting operation section 13 is operated so that the cutting sheath 8 is moved forward, the cutting sheath 8 moves forward while being guided by the inner sheath 7 and the cutting member 15 engages with the base end portion of the wire holding member 22. The distal end portion 26 of the cutting member 15 then comes up against the stopper 21 and is stopped. At this time, the suture thread 111 is cut in the vicinity of the base end side hole 25a by the cutting blade 16 which has been placed on an angle. When the suture thread 111 is cut, the inner sheath 7 and the wire holding member 22 are separated and the ligature device for medical treatment 1 and the operating device 3 are completely separated from each other. Thereafter, the wire holding member 22 naturally comes free and is discharged naturally to the outside of the body. As a result, as is shown in FIG. 41, the lesion portion W is sutured by superimposing the tissues W1 and W2 onto each other.

According to this embodiment, the same effects as those of the first embodiment can be obtained even when a lesion portion is sutured using the suture device for medical treatment 116.

Note that the present invention is not limited to the above described embodiments and may be applied to a wide range of uses.

For example, in the eighth embodiment, the cutting member 40 of the second through seventh embodiments may be used. In this case, the same effects as in each of these embodiments are obtained.

The present invention is a suture and ligature device for medical treatment that includes: a suture and ligature tool for medical treatment that has a suture and ligature member that is formed by a flexible wire material and that sutures or ligatures biological tissue, a fixing member that is able to move freely backwards and forwards relative to the suture and ligature member and that fixes biological tissue in a state in which the biological tissue is sutured or ligatured by the suture and ligature member, and a holding member through which the suture and ligature member is inserted such that it is able to move freely backwards and forwards and that has at least one aperture portion that exposes a portion of the suture and ligature member to the outside; an operating device that has a flexible sheath and a manual operating section; and a cutting member that is provided with a blade portion that is able to make at least one of a forward or backward movement and a rotational movement relatively to the suture and ligature member and that is inclined relative to the forward and backward direction or the rotational direction, and that cuts the suture and ligature member.

In this suture and ligature device for medical treatment, when the cutting member is moved forwards or backwards or is rotated, a blade portion that is placed on an inclination presses on an angle against the suture and ligature member. Because the actual blade angle is small when the blade portion presses in this manner, the suture and ligature member is cut using only a small amount of force.

In the present invention, it is also possible for a guide surface that forms a guide that causes the suture and ligature member to come up against a blade surface of the blade portion to be provided on the cutting member.

In this suture and ligature device for medical treatment, when the cutting member is moved, the guide surface is guided such that the suture and ligature member strikes the blade surface. Even if, for example, the position of the suture and ligature member does not completely match the position of the blade portion, the suture and ligature member can still be reliably cut.

In the present invention, it is also possible for the cutting member to have a first blade portion and a second blade portion that face each other, and for the first blade portion and the second blade portion to be arranged such that they approach each other at one end thereof and move away from each other at another end thereof.

In this suture and ligature device for medical treatment, the suture and ligature member is cut by being sandwiched between a pair of opposing blade portions. Because of this, it can be cut reliably using only a small amount of force.

In the present invention, it is also possible for the suture and ligature member to have exposed portions where portions of the suture and ligature member are exposed to the outside at two locations, and for the cutting member to have two blade portions that individually cut the respective exposed portions, and for these blade portions to be provided at a distance from each other in the direction of forward and backward movement of the cutting member.

In this suture and ligature device for medical treatment, in a process to move the cutting member in an axial direction, two exposed portions are cut in sequence. Compared with when two exposed portions are cut simultaneously, the cutting can be performed using a smaller amount of force.

The present invention is a suture and ligature device for medical treatment that includes: a suture and ligature tool for medical treatment that has a suture and ligature member that is formed by a flexible wire material and that sutures or ligatures biological tissue, and that has a fixing member that is able to move freely backwards and forwards relative to the suture and ligature member and that fixes biological tissue in a state in which the biological tissue is sutured or ligatured by the suture and ligature member, with the fixing member being provided with a cutting member and the cutting member having a blade portion that is inclined relative to the forward and backward direction or the rotational direction of the cutting member; and an operating device that has a flexible sheath and a manual operating section.

In this suture and ligature device for medical treatment, when the cutting member is moved forwards or backwards or is rotated, a blade portion that is placed on an inclination presses on an angle against the suture and ligature member. Because the actual blade angle is small when the blade portion presses in this manner, the suture and ligature member is cut using only a small amount of force.

The present invention is a suture and ligature device for medical treatment that includes: a suture and ligature tool for medical treatment that has a suture and ligature member that is formed by a flexible wire material and that sutures or ligatures biological tissue, a fixing member that is able to move freely backwards and forwards relative to the suture and ligature member and that fixes biological tissue in a state in which the biological tissue is sutured or ligatured by the suture and ligature member, and a holding member through which the suture and ligature member is inserted such that it is able to move freely backwards and forwards and that has at least one aperture portion that exposes a portion of the suture and ligature member to the outside; an operating device that has a flexible sheath and a manual operating section; a cutting member that is able to make at least one of a forward or backward movement and a rotational movement relatively on the suture and ligature member, and that cuts the suture and ligature member; a groove portion that is provided at a predetermined angle relative to the forward and backward direction or the rotational direction of the cutting member on either a distal end of the flexible sheath or on the holding member, or else is provided on the cutting member; and a pin that is provided such that it can slide freely inside the groove portion, wherein when the cutting member is moved forwards or backwards or is rotated relative to the operating device manually by an operator, the blade portion of the cutting member moves in a spiral at the distal end side.

In this suture and ligature device, by causing the cutting member to move in accordance with a groove and pin, the blade portion is moved in a spiral. As a result, because the blade portion presses on an angle against the suture and ligature member, the actual blade angle is small and the suture and ligature member is cut using only a small amount of force.

In the present invention, it is also possible for the suture and ligature tool for medical treatment to have an engaging member that engages the suture and ligature member in biological tissue at a distal end of the suture and ligature member, and for there to be provided a puncturing member that houses the engaging member such that the engaging member can be freely inserted therein or removed therefrom, and that punctures biological tissue.

In this suture and ligature device for medical treatment, when biological tissue is punctured by a puncturing member and is then sutured by a suture and ligature member, the blade portion is pressed on an angle against the suture and ligature member. The actual blade angle is small and the suture and ligature member is cut using only a small amount of force.

According to the present invention, because a blade portion is placed on an inclination relative to the direction of movement of a cutting member so that the actual blade angle is small when the blade portion comes against the suture and ligature member, the suture and ligature member can be cut using only a small amount of force. Because of this, the operability of a manual operating section is improved. Accordingly, it becomes possible to easily and reliably cut a suture and ligature member, thereby simplifying an operation.

What is claimed is:

1. A suture and ligature device for medical treatment comprising:

a suture and ligature tool for medical treatment that has a suture and ligature member that is formed by a flexible wire material and that sutures or ligatures biological tissue, a fixing member that is able to move freely backwards and forwards relative to the suture and ligature member and that fixes biological tissue in a state in which the biological tissue is sutured or ligatured by the suture and ligature member, and a holding member through which the suture and ligature member is inserted such that it is able to move freely backwards and forwards and that has at least one aperture portion that exposes a portion of the suture and ligature member to the outside;

an operating device that has a flexible sheath and a manual operating section; and a cutting member configured to make at least one of a forward or backward movement and a rotational movement relatively to the suture and ligature member, the cutting member comprising an inclined end portion formed at a distal end thereof, which inclined end is inclined relative to the forward and backward direction and the rotational direction and a blade portion, formed at the inclined end portion, which extends along substantially the full length of the inclined end portion, and configured to cut the suture and ligature member.

2. The suture and ligature device for medical treatment according to claim 1, wherein guide surface that forms a guide that causes the suture and ligature member to come up against a blade surface of the blade portion is provided on the cutting member.

3. The suture and ligature device for medical treatment according to claim 1, wherein the cutting member has a first blade portion and a second blade portion that face each other, and the first blade portion and the second blade portion are arranged such that they approach each other at one end thereof and move away from each other at another end thereof.

4. The suture and ligature device for medical treatment according to claim 1, wherein the suture and ligature member has exposed portions where portions of the suture and ligature member are exposed to the outside at two locations, and the cutting member has two blade portions that individually cut the respective exposed portions, and these blade portions are provided at a distance from each other in the direction of forward and backward movement of the cutting member.

5. The suture and ligature device for medical treatment according to claim 1, wherein the suture and ligature tool for medical treatment has an engaging member that engages the suture and ligature member in biological tissue at a distal end of the suture and ligature member, and there is provided a puncturing member that houses the engaging member such that the engaging member can be freely inserted therein or removed therefrom, and that punctures biological tissue.

* * * * *